United States Patent
DeAngelis

(10) Patent No.: US 7,642,071 B2
(45) Date of Patent: Jan. 5, 2010

(54) METHODS OF EXPRESSING GRAM-NEGATIVE GLYCOSAMINOGLYCAN SYNTHASE GENES IN GRAM-POSITIVE HOSTS

(75) Inventor: Paul L. DeAngelis, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 11/701,262

(22) Filed: Feb. 1, 2007

(65) Prior Publication Data

US 2007/0281342 A1 Dec. 6, 2007

Related U.S. Application Data

(63) Continuation-in-part of application No. 11/042,530, filed on Jan. 24, 2005, now Pat. No. 7,569,386, which is a continuation of application No. 09/842,484, filed on Apr. 25, 2001, now abandoned, and a continuation-in-part of application No. 09/283,402, filed on Apr. 1, 1999, now abandoned, and a continuation-in-part of application No. 09/437,277, filed on Nov. 10, 1999, now Pat. No. 6,444,447.

(60) Provisional application No. 60/765,140, filed on Feb. 2, 2006, provisional application No. 60/199,538, filed on Apr. 25, 2000.

(51) Int. Cl.
*C12P 21/04* (2006.01)
*A61K 48/00* (2006.01)

(52) U.S. Cl. ................... 435/71.1; 424/93.21

(58) Field of Classification Search ................ 435/71.1; 424/93.21

See application file for complete search history.

(56) References Cited

U.S. PATENT DOCUMENTS

| | | | |
|---|---|---|---|
| 4,511,478 A | 4/1985 | Nowinski et al. | |
| 4,585,754 A | 4/1986 | Meisner et al. | |
| 4,615,697 A | 10/1986 | Robinson | |
| 4,822,867 A | 4/1989 | Erhan | |
| 4,983,392 A | 1/1991 | Robinson | |
| 4,990,601 A | 2/1991 | Skjak-Braek et al. | |
| 5,008,253 A | 4/1991 | Casu et al. | |
| 5,171,689 A | 12/1992 | Kawaguri et al. | |
| 5,217,743 A | 6/1993 | Farah | |
| 5,337,747 A | 8/1994 | Neftel | |
| 5,472,704 A | 12/1995 | Santus et al. | |
| 5,473,034 A | 12/1995 | Yasui et al. | |
| 5,607,694 A | 3/1997 | Marx | |
| 5,610,241 A | 3/1997 | Lee et al. | |
| 5,631,019 A | 5/1997 | Marx | |
| 5,651,982 A | 7/1997 | Marx | |
| 5,711,959 A | 1/1998 | Kohler et al. | |
| 5,837,747 A | 11/1998 | Soon-Shiong et al. | |
| 5,885,609 A | 3/1999 | Amiji | |
| 5,928,667 A | 7/1999 | Rosenblatt et al. | |
| 5,945,457 A | 8/1999 | Plate et al. | |
| 5,962,136 A | 10/1999 | Dewez et al. | |
| 2003/0100534 A1 | 5/2003 | Zoppetti et al. | |
| 2005/0164984 A1 | 7/2005 | DeAngelis | |

FOREIGN PATENT DOCUMENTS

| | | |
|---|---|---|
| EP | 01304338 | 4/2003 |
| JP | WO 03/012099 | 2/2003 |
| WO | WO 88/05821 | 8/1988 |
| WO | WO 95/24497 | 9/1995 |
| WO | WO 97/20061 | 6/1997 |
| WO | WO 00/27437 | 5/2000 |
| WO | WO 01/02597 | 1/2001 |
| WO | WO 01/80810 | 11/2001 |

OTHER PUBLICATIONS

"Differences in the Effects of pH on the Hydrolytic and Transgalactosylic Reactions of Beta-Galactosidase (*Escherichia coli*)", Huber et al., Can. J. Biochem. Cell Biol., 61:198-206 (1983).
"Binding and Reactivity at the 'Glucose' Site of Galactosyl-Beta-Galactosidase (*Escherichia coli*)", Huber et al., Arch Biochem Biophys., 234: 151-160 (1984).
"Effect of Replacing Uridine 33 in Yeast tRNAPhe on the Reaction With Ribosomes", Dix et al., J. Biol. Chem., 261(22):10112-8 (1986).
"Structure and Serological Characteristics of the Capsular K4 Antigen of *Escherichia coli* O5:K4:H4, A Fructose-Containing Polysaccharide With a Chondroitin Backbone", Rodriguez et al., Eur. J. Biochem., 177:117-124 (1988).
"The Carboxy-Terminal Domain of the LexA Repressor Oligomerises Essentially as the Entire Protein", Schnarr et al., FEBS Lett., 234:56-60 (1988).
"A Cryptic Fimbrial Gene in Serratia Marcescens", Moriya et al., J. Bacteriol., 171(12): 6629-36 (1989).
"Monoclonal Antibodies Specific for K88ab, K88ac and K88ad Antigens of *Escherichia coli*", Li et al., Wei Sheng Wu Xue Bao, 29:348-353 (1989) (Full Article Unavailable; Abstract Only).
"Kinetic Characterization of the Unisite Catalytic Pathway of Seven Beta-Subunit Mutant F1-ATPases From *Escherichia coli*", al-Shawi et al., J. Biol. Chem., 264(26): 15376-83 (1989).
"Slow-Binding Inhibition of the *Escherichia coli* Pyruvate Dehydrogenase Multienzyme Complex by Acetylphosphinate", Schonbrunn-Hanebeck et al., Biochemistry, 29(20): 4880-5 (1990).
"Molecular Cloning and Expression of the Genes Encoding the *Escherichia coli* K4 Capsular Polysaccharide, A Fructose-Substituted Chondroitin", Drake et al., FEMS Microbiol. Lett., 54(1-3):227-30 (1990) (Full Article Unavailable; Abstract Only).

(Continued)

*Primary Examiner*—Valarie Bertoglio
*Assistant Examiner*—David Montanari
(74) *Attorney, Agent, or Firm*—Dunlap Codding, P.C.

(57) ABSTRACT

The present invention relates to a Gram-negative glycosaminoglycan gene and methods of making and using same. The present invention relates to recombinant Gram-positive host cells containing a Gram-negative glycosaminoglycan synthase gene, and methods of producing glycosaminoglycans using such recombinant host cells.

19 Claims, 5 Drawing Sheets

OTHER PUBLICATIONS

Figure 1:
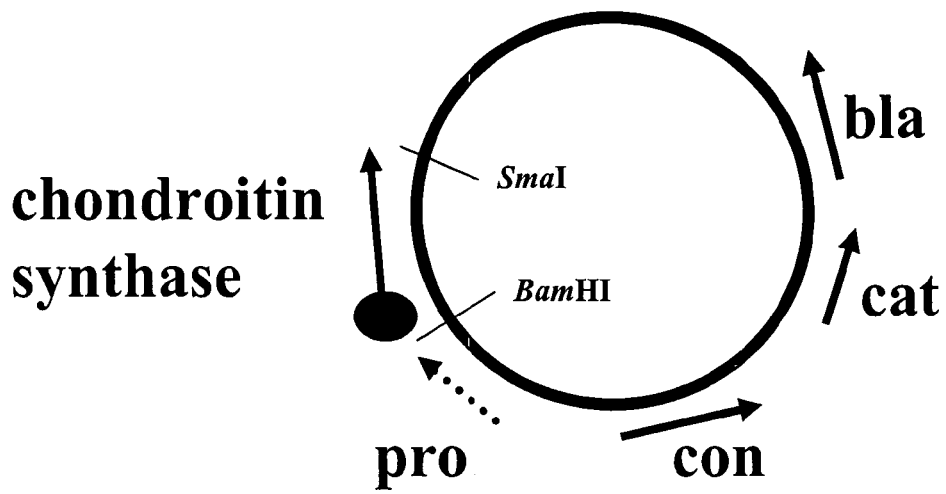
Figure 1:
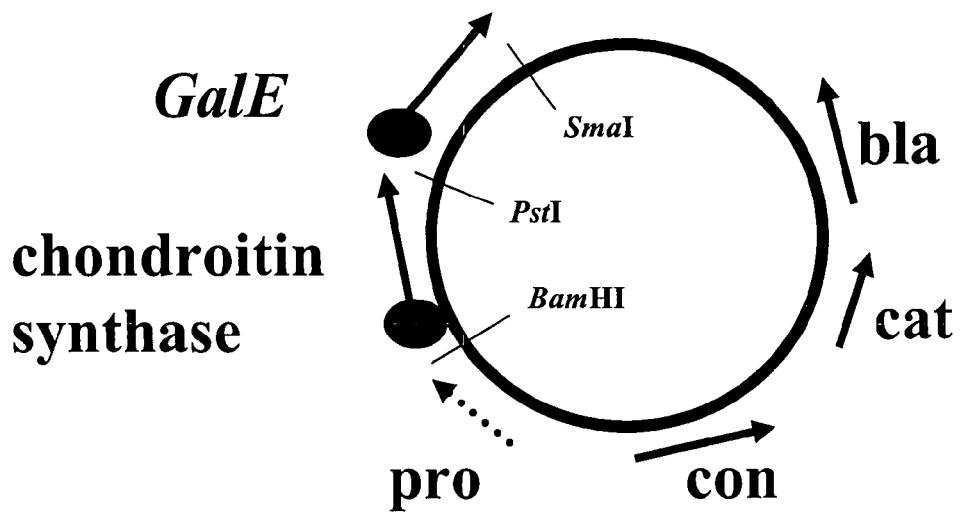
Figure 1:

"Electron Microscopic Study of Coexpression of Adhesive Protein Capsules and Polysaccharide Capsules in *Escherichia coli*", Kronke et al., Infect. Immunity, 58:2710-4 (1991).

"Transport and Utilization of Ferrioxamine-E-Bound Iron in Erwinia Herbicola (Pantoea agglomerans)", Matzanke et al., Biol. Met., 181-185 (1991).

"Modulation of the Tight Binding of Carboxyarabinitol 1, 5-Biphosphate to the Large Subunit of Ribulose 1,5-Bisphosphate Carboxylase/Oxygenase", Smrcka et al., Arch. Biochem. Biophys., 286: 14-9 (1991).

"Slow-Onset Inhibition of Ribosomal Peptidyltransferase by Lincomycin", Kallia-Raftopoulos et al., Arch. Biochem. Biophys., 298: 332-339 (1992).

"Enhanced Catalysis by Active-Site Mutagenesis at Aspartic Acid 153 in *Escherichia coli* Alkaline Phosphatase", Matlin et al., Biochemistry, 31(35): 8196-8200 (1992).

"A Study of Vitamin Inhibition on the Mutagenicity of the Antineoplastic Drugs", Zhao and Huang, Zhonghua Yu Fang Yi Xue Za Zhi, 26:291-293 (1992) (Full Article Unavailable; Abstract Only).

"Molecular Cloning of a Gene Coding for Beta-Glucanase From *Bacillus subtilis* K4, Antagonist to Plant Pathogenic Fungi", Kim et al., RDA Journal of Agricultural Science Biotechnology, 35(1): 213-218 (1993).

"Preliminary Study of Test Methods to Assess the Virucidal Activity of Skin Disinfectants Using Poliovirus and Bacteriophages", Davies et al., Journal of Hospital Infection, 25(2): 125-131 (1993).

"The *Escherichia coli* serA-Linked Capsule Locus and its Flanking Sequences are Polymorphic, Genetic Evidence for the Existence of More Than Two Groups of Capsule Gene Clusters", Drake et al., J. Gen. Microbiol., 139 (Pt. 8): 1707-1714 (1993).

"Reaction of Modified and Unmodified tRNA (Tyr) Substrates With Tyrosyl-tRNA Synthetase (*Bacillus stearothermophilus*)", Avis et al., Biochemistry, 32(20): 5312-5320 (1993).

"Effect of pH on Solubility and Ionic State of Lipopolysaccharide Obtained From the Deep Rough Mutant of *Escherichia coli*", Din et al., Biochemistry, 32(17): 4579-4586 (1993).

"Amino Acid Residues of the Kringle-4 and Kringle-5 Domains of Human Plasminogen That Stabilize Their Interactions With Omega-Amino Acid Ligands", McCance et al., J. Biol. Chem., 269(51):32405-32410 (1994).

"Enzymic Reconstruction of Glycosaminoglycan Oligosaccharide Chains Using the Transglycosylation Reaction of Bovine Testicular Hyaluronidase", Saitoh, et al., The American Society for Biochemistry and Molecular Biology, Inc., vol. 270, No. 8, pp. 3741-3747 (1995).

"Kinetic Mechanism of Kinesin Motor Domain", Ma and Taylor, Biochemistry, 34(40): 13233-13241 (1995).

"Production and Purification of an Extracellularly Produced K4 Polysachharide From *Escherichia coli*", Manzoni et al., Biotechnol. Lett., 18(4): 383-386 (1996).

"A Novel Family of Phospholipase D Homologues That Includes Phospholipid Synthases and Putative Endonucleases: Identification of Duplicated Repeats and Potential Active Site Residues", Ponting and Kerr, Protein Science, 914-922 (May 1996).

"Biosynthesis of Dermatan Sulphate. Defructosylated *Escherichia coli* K4 Capsular Polysaccharide as a Substrate for the D-Glucuronyl C-5 Epimerase, and an Indication of a Two-Base Reaction Mechanism", Hannesson et al., Biochem. J., 313(Pt. 2): 589-596 (1996).

"Biosynthesis of the *Escherichia coli* K4 Capsule Polysaccharide: A Parallel System for Studies of Glycosyltransferases in Chondroitin Formation", Lidholt et al., J. Biol. Chem., 272(5):2682-2687 (1997).

"Enzymological Characterization of the Pasteurella Multocida Hyaluronic Acid Synthase", DeAngelis, Biochemistry, vol. 35, No. 30, pp. 9768-9771 (1996).

"Kinetic Mechanism of Monomeric Non-Claret Disjunctional Protein (Ncd) ATPase", Pechatnikova et al., J. Biol. Chem., 272(49): 30735-30740 (1997).

"A Two-Site Mechanism for ATP Hydrolysis by the Asymmetric Rep Dimer P2S as Revealed by Site-Specific Inhibition With ADP-A1F4", Wong and Lohman, Biochemistry, 36(11): 3115-3125 (1997).

"The Capsule Biosynthetic Locus of *Pasturella multocida* A:1", Chung et al., FEMS Microbiology Letters, 186:289-296 (1998).

"Identification and Molecular Cloning of a Unique Hyaluronan Synthase From *Pasteurella multocida*", DeAngelis, et al., J. Biol. Chem., vol. 273, Issue 14, pp. 8454-8458 (1998).

"Role of Fimbriae-Mediated Adherence for Neutrophil Migration Across *Escherichia coli*-Infected Epithelial Cell Layers", Godaly et al., Molecular Microbiology, 30(4): 725-735 (1998).

"Complete Kinetic Mechanism of Elongation Factor Tu-Dependent Binding of Aminoacyl-tRNA to the a Site of the *E. coli* Ribosome", Pape et al., EMBO J., 17(24): 7490-7497 (1998).

"Glycosidases and Glycosyl Transferases in Glycoside and Oligosaccharide Synthesis", Crout, et al., Current Opinion in Chemical Biology, pp. 2:98-111 (1998).

"Enzymatic Reconstruction of a Hybrid Glycosaminoglycan Containing 6-Sulfated, 4-Sulfated, and Unsulfated N-Acetylgalactosamine", Takagaki, et al., Biochemical and Biophysical Research Communications 258, pp. 741-744 (1999).

"Transfer RNA Identity Contributes to Transition State Stabilization During Aminoacyl-tRNA Synthesis", Ibba et al., Nucleic Acids Research, 27(18):3631-3637 (1999).

"Contractile Function and Myoplasmic Free Ca2+ (Cam) in Coronary and Mesenteric Arteries of Endotoxemic Guinea Pigs", Jones et al., Shock, 11: 64-71 (1999). (Full Article Unavailable; Abstract Only).

"Biomimetic Transport and Rational Drug Delivery", Ranney, et al., Biochemical Pharmacology, vol. 59, pp. 105-114 (2000).

"Chimeric Glycosaminoglycan Oligosaccharides Synthesized by Enzymatic Reconstruction and Their Use in Substrate Specificity Determination of *Streptococcus hyaluronidase*", Takagaki, et al., J. Biochem. vol. 127, pp. 695-702 (2000).

"Genetic Mapping of the K1 and K4 Antigens (L) of *Escherichia coli*. Non-Allelism of K(L) Antigens With K Antigens of O8:K27(A), O8:K8 (L) and O9:K57 (B)", Orskov et al., Acta Pathol Microbiol Scand B, 84:125-131 (1976).

"A Terminal 6-Sulfotransferase Catalyzing a Synthesis of N-Acetylgalactosamine 4,6-Bissulfate Residue At The Nonreducing Terminal Position of Chondroitin Sulfate" Nakanishi et al. The Journal of Biological Chemistry 1981, 256 (11) 5443-5449).

"Kinetic Studies on the Interaction Between a Ribosomal Complex Active in Peptide Bond Formation and the Macrolide Antibiotics Tylosin and Erythromycin", Dinos et al., Biochemistry, 39(38): 11621-11628 (2000).

"Structure-Function Relationships in Novel Peptide Dodecamers With Broad-Spectrum Bactericidal and Endotoxin-Neutralizing Activities", Mayo et al., Biochemical Journal, 349(3): 717-728 (2000).

Identification and Molecular Cloning of a Chondroitin Synthase From *Pasteurella multocida* Type F, Paul DeAngelis, et al., Journal of Biological Chemistry, vol. 275, No. 31, pp. 24124-24129, Apr. 2000.

"Subunit Communication in Tetrameric Class 2 Human Liver Aldehyde Dehydrogenase as the Basis for Half-of-The-Site Reactivity and the Dominance of the Oriental Subunit in a Heterotetramer", Weiner et al., Chemico-Biological Interactions, 130-132(1-3):47-56 (2001).

Molecular Cloning and Expression of a Human Chondroitin Synthase, Hiroshi Kitagawa, et al., Journal of Biological Chemistry, vol. 276, No. 42, pp. 38721-38726, Aug. 2001.

Utility of Molecularly Dissected Synthases for Chemoenzymatic Synthesis of Glycosaminoglycan Oligosaccharides, Paul DeAngelis, Glycobiology, vol. 11, No. 10, pp. 934, Oct. 2001.

"Detection of Submicrogram Quantities of Glycosaminoglycans on Agarose Gels by Sequential Staining With Toluidine Blue and Stains-All", Volpi and Maccari, Electrophoresis, 23(24):4060-4066 (2002).

Keratan Sulfate Biosynthesis, James Funderburqh, IUBMB Life, vol. 54, pp. 187-194, 2002.

Mammalian Hyaluronan Synthases, Naoki Itano, et al., IUBMB Life, vol. 54, pp. 195-199, 2002.

Molecular Cloning and Expression of Human Chondroitin N-Acetylgalactosaminyltransferase, Toru Uyama, et al. Journal of Biological Chemistry, vol. 277, No. 11, pp. 8841-8846, Jan. 2002.

Molecular Cloning and Characterization of Chondroitin Polymerase From *Escherichia coli* Strain K4, Toshio Ninomiya, et al., Journal of Biological Chemistry, vol. 277, No. 24, pp. 21567-21575, Apr. 2002.

Molecular Cloning and Characterization of a Novel Chondroitin Sulfate Glucuronyltransferase That Transfers Glucuronic Acid to N-Acetylgalactosamine, Masanori Gotoh, et al., Journal of Biological Chemistry, vol. 277, No. 41, pp. 38179-38188, Jul. 2002.

Structure Function Analysis of Pasteurella Glycosaminoglycan Synthesis, Wei Jing, et al., Glycobiology, vol. 12, No. 10, pp. 705, Oct. 2002.

Biosynthesis of Chondroitin/Dermatan Sulfate, Jeremiah Silbert, et al., IUBMB Life, vol. 54, pp. 177-186, Oct. 2002.

Functional Characteristics and Catalytic Mechanisms of the Bacterial Hyaluronan Synthases, Paul Weigel, IUBMB Life, vol. 54, pp. 201-211, Oct. 2002.

"Structural/Functional Characterization of the Alpha 2-Plasmin Inhibitor C-Terminal Peptide", Frank et al., Biochemistry, 42:1078-1085 (2003).

"Trp-999 of Beta-Galactosidase (*Escherichia coli*) is a Key Residue for Binding, Catalysis, and Synthesis of Allolactose, The Natural LAC Operon Inducer", Huber et al., Biochemistry, 42(6): 1796-1803 (2003).

"Separation of Capsular Polysaccharide K4 and Defructosylated K4 Derived Disaccharides by High-Performance Capillary Electrophoresis and High-Performance Liquid Chromatography", Volpi, Electrophoresis, 24(6): 1063-1068 (2003).

"Milligram-Scale Preparation and Purification of Oligosaccharides of Defined Length Possessing the Structure of Chondroitin From Defructosylated Capsular Polysaccharide K4", Volpi, Glycobiology, 13(9):635-640 (2003).

N   B. *subtilis* A168 (pHCM04) = NO insert control
S   HA standards (Hi- & LoLadder, Hyalose LLC)
1   B. *subtilis* A168 (pHCM04/pmCS)
2   B. *subtilis* A168 (pHCM04 /pmCS-GalE)
3   B. *subtilis* A168 (pHCM04 /pmCS-GalE)

4   B. subtilis A168 (pHCM05/pmCS-GalE)
N   B. subtilis A168 (pHCM05) Vector alone = 'no insert' control
S   HA standard ladders (Hyalose LLC)
HA  authentic HA from recombinant Bacillus B   Bacillus-derived chondroitin sample
HA  authentic HA (Streptococcus)
C   authentic chondroitin (Pasteurella)

SEQUENCE LISTING

<160> NUMBER OF SEQ ID NOS: 2

<210> SEQ ID NO 1
<211> LENGTH: 2979

-continued

<212> TYPE: DNA
<213> ORGANISM: Pasteurella multocida

<400> SEQUENCE: 1

```
ttataaactg attaaagaag gtaaacgatt caagcaaggt taatttttaa aggaaagaaa     60
atgaatacat tatcacaagc aataaaagca tataacagca atgactatga attagcactc    120
aaattatttg agaagtctgc tgaaacctac gggcgaaaaa tcgttgaatt ccaaattatc    180
aaatgtaaag aaaaactctc gaccaattct tatgtaagtg aagataaaaa aaacagtgtt    240
tgcgatagct cattagatat cgcaacacag ctcttacttt ccaacgtaaa aaaattaact    300
ctatccgaat cagaaaaaaa cagtttaaaa aataaatgga aatctatcac tgggaaaaaa    360
tcggagaacg cagaaatcag aaaggtggaa ctagtaccca aagattttcc taaagatctt    420
gttcttgctc cattgccaga tcatgttaat gattttacat ggtacaaaaa tcgaaaaaaa    480
agcttaggta taaagcctgt aaataagaat atcggtcttt ctattattat tcctacattt    540
aatcgtagcc gtattttaga tataacgtta gcctgtttgg tcaatcagaa aacaaactac    600
ccatttgaag tcgttgttgc agatgatggt agtaaggaaa acttacttac cattgtgcaa    660
aaatacgaac aaaaacttga cataaagtat gtaagacaaa aagattatgg atatcaattg    720
tgtgcagtca gaaacttagg tttacgtaca gcaaagtatg attttgtctc gattctagac    780
tgcgatatgg caccacaaca attatgggtt cattcttatc ttacagaact attagaagac    840
aatgatattg ttttaattgg acctagaaaa tatgtggata ctcataatat taccgcagaa    900
caattcctta acgatccata tttaatagaa tcactacctg aaaccgctac aaataacaat    960
ccttcgatta catcaaaagg aaatatatcg ttggattgga gattagaaca tttcaaaaaa   1020
accgataatc tacgtctatg tgattctccg tttcgttatt ttagttgcgg taatgttgca   1080
ttttctaaag aatggctaaa taaagtaggt tggttcgatg aagaatttaa tcattggggg   1140
ggcgaagatg tagaatttgg ttacagatta tttgccaaag gctgtttttt cagagtaatt   1200
gacggcggaa tggcatacca tcaagaacca cctggtaaag aaaatgaaac agaccgcgaa   1260
gctggtaaaa gtattacgct taaaattgtg aaagaaaagg taccttacat ctatagaaag   1320
cttttaccaa tagaagattc acatattcat agaatacctt tagtttctat ttatatcccc   1380
gcttataact gtgcaaatta tattcaaaga tgtgtagata gtgctcttaa tcaaactgtt   1440
gtcgatctcg aggtttgtat ttgtaacgat ggttcaacag ataatacctt agaagtgatc   1500
aataagcttt atggtaataa tcctagggta cgcatcatgt ctaaaccaaa tggcggaata   1560
gcctcagcat caaatgcagc cgtttctttt gctaaaggtt attacattgg gcagttagat   1620
tcagatgatt atcttgagcc tgatgcagtt gaactgtgtt taaaagaatt tttaaaagat   1680
aaaacgctag cttgtgttta taccactaat agaaacgtca atccggatgg tagcttaatc   1740
gctaatggtt acaattggcc agaattttca cgagaaaaac tcacaacggc tatgattgct   1800
caccatttta gaatgtttac gattagagct tggcatttaa cggatggatt taacgaaaat   1860
attgaaaacg ccgtggatta tgacatgttc cttaaactca gtgaagttgg aaaatttaaa   1920
catcttaata aaatctgcta taaccgcgta ttacatggtg ataacacatc cattaagaaa   1980
ctcggcattc aaaagaaaaa ccattttgtt gtagtcaatc agtcattaaa tagacaaggc   2040
atcaattatt ataattatga caaatttgat gatttagatg aaagtagaaa gtatatcttc   2100
aataaaaccg ctgaatatca agaagaaatg gatattttaa aagatcttaa actcattcaa   2160
aataaagatg ccaaaatcgc agtcagtatt ttctatccca atacattaaa cggcttagtg   2220
```

-continued

```
aaaaaactaa acaatattat tgaatataat aaaaatatat tcgttattat tctacatgtt   2280
gataagaatc atcttacacc agacatcaaa aaagaaatat tggctttcta tcataagcac   2340
caagtgaata ttttactaaa taatgacatc tcatattaca cgagtaatag actaataaaa   2400
actgaggcac atttaagtaa tattaataaa ttaagtcagt taaatctaaa ttgtgaatac   2460
atcatttttg ataatcatga cagcctattc gttaaaaatg acagctatgc ttatatgaaa   2520
aaatatgatg tcggcatgaa tttctcagca ttaacacatg attggatcga gaaaatcaat   2580
gcgcatccac catttaaaaa gctgattaaa acctatttta atgacaatga cttaagaagt   2640
atgaatgtga aaggggcatc acaaggtatg tttatgaagt atgcgctacc gcatgagctt   2700
ctgacgatta ttaaagaagt catcacatcc tgccaatcaa ttgatagtgt gccagaatat   2760
aacactgagg atatttggtt ccaatttgca cttttaatct tagaaaagaa aaccggccat   2820
gtatttaata aaacatcgac cctgacttat atgccttggg aacgaaaatt acaatggaca   2880
aatgaacaaa ttcaaagtgc aaaaaaaggc gaaaatatcc ccgttaacaa gttcattatt   2940
aatagtataa cgctataaaa catttgcatt ttattaaaa                          2979
```

<210> SEQ ID NO 2
<211> LENGTH: 965
<212> TYPE: PRT
<213> ORGANISM: Pasteurella multocida

<400> SEQUENCE: 2

```
Met Asn Thr Leu Ser Gln Ala Ile Lys Ala Tyr Asn Ser Asn Asp Tyr
1               5                   10                  15

Glu Leu Ala Leu Lys Leu Phe Glu Lys Ser Ala Glu Thr Tyr Gly Arg
            20                  25                  30

Lys Ile Val Glu Phe Gln Ile Ile Lys Cys Lys Glu Lys Leu Ser Thr
        35                  40                  45

Asn Ser Tyr Val Ser Glu Asp Lys Lys Asn Ser Val Cys Asp Ser Ser
    50                  55                  60

Leu Asp Ile Ala Thr Gln Leu Leu Leu Ser Asn Val Lys Lys Leu Thr
65                  70                  75                  80

Leu Ser Glu Ser Glu Lys Asn Ser Leu Lys Asn Lys Trp Lys Ser Ile
                85                  90                  95

Thr Gly Lys Lys Ser Glu Asn Ala Glu Ile Arg Lys Val Glu Leu Val
            100                 105                 110

Pro Lys Asp Phe Pro Lys Asp Leu Val Leu Ala Pro Leu Pro Asp His
        115                 120                 125

Val Asn Asp Phe Thr Trp Tyr Lys Asn Arg Lys Lys Ser Leu Gly Ile
    130                 135                 140

Lys Pro Val Asn Lys Asn Ile Gly Leu Ser Ile Ile Ile Pro Thr Phe
145                 150                 155                 160

Asn Arg Ser Arg Ile Leu Asp Ile Thr Leu Ala Cys Leu Val Asn Gln
                165                 170                 175

Lys Thr Asn Tyr Pro Phe Glu Val Val Val Ala Asp Asp Gly Ser Lys
            180                 185                 190

Glu Asn Leu Leu Thr Ile Val Gln Lys Tyr Glu Gln Lys Leu Asp Ile
        195                 200                 205

Lys Tyr Val Arg Gln Lys Asp Tyr Gly Tyr Gln Leu Cys Ala Val Arg
    210                 215                 220

Asn Leu Gly Leu Arg Thr Ala Lys Tyr Asp Phe Val Ser Ile Leu Asp
225                 230                 235                 240
```

```
Cys Asp Met Ala Pro Gln Gln Leu Trp Val His Ser Tyr Leu Thr Glu
            245                 250                 255
Leu Leu Glu Asp Asn Asp Ile Val Leu Ile Gly Pro Arg Lys Tyr Val
        260                 265                 270
Asp Thr His Asn Ile Thr Ala Glu Gln Phe Leu Asn Asp Pro Tyr Leu
            275                 280                 285
Ile Glu Ser Leu Pro Glu Thr Ala Thr Asn Asn Pro Ser Ile Thr
    290                 295                 300
Ser Lys Gly Asn Ile Ser Leu Asp Trp Arg Leu His Phe Lys Lys
305                 310                 315                 320
Thr Asp Asn Leu Arg Leu Cys Asp Ser Pro Phe Arg Tyr Phe Ser Cys
                325                 330                 335
Gly Asn Val Ala Phe Ser Lys Glu Trp Leu Asn Lys Val Gly Trp Phe
            340                 345                 350
Asp Glu Glu Phe Asn His Trp Gly Gly Glu Asp Val Glu Phe Gly Tyr
        355                 360                 365
Arg Leu Phe Ala Lys Gly Cys Phe Phe Arg Val Ile Asp Gly Gly Met
    370                 375                 380
Ala Tyr His Gln Glu Pro Pro Gly Lys Glu Asn Glu Thr Asp Arg Glu
385                 390                 395                 400
Ala Gly Lys Ser Ile Thr Leu Lys Ile Val Lys Glu Lys Val Pro Tyr
                405                 410                 415
Ile Tyr Arg Lys Leu Leu Pro Ile Glu Asp Ser His Ile His Arg Ile
            420                 425                 430
Pro Leu Val Ser Ile Tyr Ile Pro Ala Tyr Asn Cys Ala Asn Tyr Ile
        435                 440                 445
Gln Arg Cys Val Asp Ser Ala Leu Asn Gln Thr Val Val Asp Leu Glu
    450                 455                 460
Val Cys Ile Cys Asn Asp Gly Ser Thr Asp Asn Thr Leu Glu Val Ile
465                 470                 475                 480
Asn Lys Leu Tyr Gly Asn Asn Pro Arg Val Arg Ile Met Ser Lys Pro
                485                 490                 495
Asn Gly Gly Ile Ala Ser Ala Ser Asn Ala Ala Val Ser Phe Ala Lys
            500                 505                 510
Gly Tyr Tyr Ile Gly Gln Leu Asp Ser Asp Asp Tyr Leu Glu Pro Asp
        515                 520                 525
Ala Val Glu Leu Cys Leu Lys Glu Phe Leu Lys Asp Lys Thr Leu Ala
    530                 535                 540
Cys Val Tyr Thr Thr Asn Arg Asn Val Asn Pro Asp Gly Ser Leu Ile
545                 550                 555                 560
Ala Asn Gly Tyr Asn Trp Pro Glu Phe Ser Arg Glu Lys Leu Thr Thr
                565                 570                 575
Ala Met Ile Ala His His Phe Arg Met Phe Thr Ile Arg Ala Trp His
            580                 585                 590
Leu Thr Asp Gly Phe Asn Glu Asn Ile Glu Asn Ala Val Asp Tyr Asp
        595                 600                 605
Met Phe Leu Lys Leu Ser Glu Val Gly Lys Phe Lys His Leu Asn Lys
    610                 615                 620
Ile Cys Tyr Asn Arg Val Leu His Gly Asp Asn Thr Ser Ile Lys Lys
625                 630                 635                 640
Leu Gly Ile Gln Lys Lys Asn His Phe Val Val Asn Gln Ser Leu
                645                 650                 655
Asn Arg Gln Gly Ile Asn Tyr Tyr Asn Tyr Asp Lys Phe Asp Asp Leu
```

-continued

```
                    660                 665                 670
Asp Glu Ser Arg Lys Tyr Ile Phe Asn Lys Thr Ala Glu Tyr Gln Glu
            675                 680                 685
Glu Met Asp Ile Leu Lys Asp Leu Lys Leu Ile Gln Asn Lys Asp Ala
        690                 695                 700
Lys Ile Ala Val Ser Ile Phe Tyr Pro Asn Thr Leu Asn Gly Leu Val
705                 710                 715                 720
Lys Lys Leu Asn Asn Ile Ile Glu Tyr Asn Lys Asn Ile Phe Val Ile
                725                 730                 735
Ile Leu His Val Asp Lys Asn His Leu Thr Pro Asp Ile Lys Lys Glu
            740                 745                 750
Ile Leu Ala Phe Tyr His Lys His Gln Val Asn Ile Leu Leu Asn Asn
            755                 760                 765
Asp Ile Ser Tyr Tyr Thr Ser Asn Arg Leu Ile Lys Thr Glu Ala His
        770                 775                 780
Leu Ser Asn Ile Asn Lys Leu Ser Gln Leu Asn Leu Asn Cys Glu Tyr
785                 790                 795                 800
Ile Ile Phe Asp Asn His Asp Ser Leu Phe Val Lys Asn Asp Ser Tyr
                805                 810                 815
Ala Tyr Met Lys Lys Tyr Asp Val Gly Met Asn Phe Ser Ala Leu Thr
            820                 825                 830
His Asp Trp Ile Glu Lys Ile Asn Ala His Pro Pro Phe Lys Lys Leu
        835                 840                 845
Ile Lys Thr Tyr Phe Asn Asp Asn Asp Leu Arg Ser Met Asn Val Lys
    850                 855                 860
Gly Ala Ser Gln Gly Met Phe Met Lys Tyr Ala Leu Pro His Glu Leu
865                 870                 875                 880
Leu Thr Ile Ile Lys Glu Val Ile Thr Ser Cys Gln Ser Ile Asp Ser
                885                 890                 895
Val Pro Glu Tyr Asn Thr Glu Asp Ile Trp Phe Gln Phe Ala Leu Leu
            900                 905                 910
Ile Leu Glu Lys Lys Thr Gly His Val Phe Asn Lys Thr Ser Thr Leu
        915                 920                 925
Thr Tyr Met Pro Trp Glu Arg Lys Leu Gln Trp Thr Asn Glu Gln Ile
    930                 935                 940
Gln Ser Ala Lys Lys Gly Glu Asn Ile Pro Val Asn Lys Phe Ile Ile
945                 950                 955                 960
Asn Ser Ile Thr Leu
            965
```

METHODS OF EXPRESSING GRAM-NEGATIVE GLYCOSAMINOGLYCAN SYNTHASE GENES IN GRAM-POSITIVE HOSTS

CROSS-REFERENCE TO RELATED APPLICATIONS

This application claims benefit under 35 U.S.C. 119(e) of U.S. Ser. No. 60/765,140, filed Feb. 2, 2006. This application is a continuation-in-part of U.S. Ser. No. 11/042,530 now U.S. Pat. No. 7,569,386, filed Jan. 24, 2005; which is a continuation of U.S. Ser. No. 09/842,484 filed Apr. 25, 2001, now abandoned, which claims benefit under 35 U.S.C. 119(e) of provisional application U.S. Ser. No. 60/199,538, filed Apr. 25, 2000. Said U.S. Ser. No. 09/842,484 is also a continuation-in-part of U.S. Ser. No. 09/283,402, filed Apr. 1, 1999, now abandoned; and said U.S. Ser. No. 09/842,484 is also a continuation-in-part of U.S. Ser. No. 09/437,277, filed Nov. 10, 1999, now U.S. Pat. No. 6,444,447, issued Sep. 3, 2002. The contents of each of the above-referenced patents and patent applications are hereby expressly incorporated herein by reference in their entirety.

STATEMENT REGARDING FEDERALLY FUNDED RESEARCH

The government owns certain rights in the present invention pursuant to a grant from the National Institutes of Health (GM56497) and a grant from the National Science Foundation (MCB-9876193).

BACKGROUND OF THE INVENTION

1. Field of the Invention

The present invention relates to a chondroitin synthase gene and methods of making and using same. In more particular, but not by way of limitation, the present invention relates to a chondroitin synthase gene from *Pasteurella multocida* and methods of using same in a gram-positive host.

2. Background Information Relating to the Invention

Glycosaminoglycans [GAGs] are long linear polysaccharides consisting of disaccharide repeats that contain an amino sugar and are found in most animals. Chondroitin $[\beta(1,4)\text{GlcUA-}\beta(1,3)\text{GalNAc}]_n$, heparin/heparan $[\alpha(1,4)\text{GlcUA-}\beta(1,4)\text{GlcNAc}]_n$, and hyaluronan $[\beta(1,4)\text{GlcUA-}\beta(1,3)\text{GlcNAc}]_n$ are the three most prevalent GAGs found in humans. Chondroitin and heparin in animals typically have n=20 to 100, while hyaluronan typically has $n=10^3$. Chondroitin and heparin are synthesized as glycoproteins and are sulfated at various positions in vertebrates. Hyaluronan is not sulfated in vertebrates. A substantial fraction of the GlcUA residues of heparin and chondroitin are epimerized to form iduronic acid.

Many lower animals possess these same GAGs or very similar molecules. GAGs play both structural and recognition roles on the cell surface and in the extracellular matrix. By virtue of their physical characteristics, namely a high negative charge density and a multitude of polar hydroxyl groups, GAGs help hydrate and expand tissues. Numerous proteins bind selectively to one or more of the GAGs. Thus the proteins found on cell surfaces or the associated extracellular matrices (e.g., CD44, collagen, fibronectin) of different cell types may adhere or interact via a GAG intermediate. Also GAGs may sequester or bind certain proteins (e.g. growth or coagulation factors) to cell surfaces.

Certain pathogenic bacteria produce an extracellular polysaccharide coating, called a capsule, which serves as a virulence factor. In a few cases, the capsule is composed of GAG or GAG-like polymers. As the microbial polysaccharide is identical or very similar to the host GAG, the antibody response is either very limited or non-existent. The capsule is thought to assist in the evasion of host defenses such as phagocytosis and complement. Examples of this clever strategy of molecular camouflage are the production of an authentic HA polysaccharide by Gram-negative Type A *Pasteurella multocida* and Gram-positive Group A and C *Streptococcus*. The HA capsule of these microbes increases virulence by $10^2$ to $10^3$-fold as measured by $LD_{50}$ values, the number of colony forming units that will kill 50% of the test animals after bacterial challenge.

The invasiveness and pathogenicity of certain *E. coli* strains has also been attributed to their polysaccharide capsules. Two *Escherichia coli* capsular types, K4 and K5, make polymers composed of GAG-like polymers. The *E. coli* K4 polymer is an unsulfated chondroitin backbone decorated with fructose side-branches on the C3 position of the GlcUA residues. The *E. coli* K5 capsular material is a polysaccharide, called heparosan, identical to mammalian heparin except that the bacterial polymer is unsulfated and there is no epimerization of GlcUA to iduronic acid.

The studies of GAG biosynthesis have been instrumental in understanding polysaccharide production in general. The HA synthases were the first GAG glycosyltransferases to be identified at the molecular level. These enzymes utilize UDP-sugar nucleotide substrates to produce large polymers containing thousands of disaccharide repeats. The genes encoding bacterial, vertebrate, and viral HAS enzymes have been cloned. In all these cases, expression studies demonstrated that transformation with DNA encoding a single HAS polypeptide conferred the ability of foreign hosts to synthesize HA. Except for the most recent HAS to be identified, *P. multocida* PmHAS, these proteins have similar amino acid sequences and predicted topology in the membrane. Two classes of HASs have been proposed to exist based on these structural differences as well as potential differences in reaction mechanism The biochemical study of chondroitin biosynthesis in vertebrates was initiated in the 1960s. Only recently have the mammalian enzymes for elongation of the polysaccharide backbone of chondroitin been tentatively identified by biochemical means. An 80-kDa GlcUA transferase found in vertebrate cartilage and liver was implicated in the biosynthesis of the chondroitin backbone by photoaffinity labeling with an azidoUDP-GlcUA probe. A preparation from bovine serum with the appropriate GalNAc- and GlcUA-transferase activities in vitro was obtained by conventional chromatography, but several bands on SDS polyacrylamide gels (including a few migrating ~80 kDa) were observed. Several genes called ChSy have been recently identified that encode the enzymes that polymerize the chondroitin backbone in animals and humans; these proteins are not homologous to the *Pasteurella* PmCS gene described herein.

Chondroitin polysaccharide $([\beta(1,3)\text{GalNAc-}\beta(1,4)\text{GlcUA}]_n$; where n=~10-2000) has use as a hyaluronan (HA) polysaccharide substitute in medical or cosmetic applications. Both chondroitin and hyaluronan form viscoelastic gels (suitable for eye or joint applications) or hydrophilic, hygroscopic materials (suitable for moisturizer or wound dressings). Unmodified or underivatized chondroitin is not known to exist or, if present, in very small quantities in the human body. The main advantage is that byproducts of natural HA degradation (by shear, enzyme, radical or oxidation processes) have certain biological activities with respect to vascularization, angiogenesis, cancer, tissue modulation, but similar byproducts of chondroitin (in the proposed unsulfated, unmodified state) may not have the same biological activity. The chondroitin polymers are more inert, loosely speaking, than the analogous HA molecule. Chondroitin from either *P. multocida* Type F or a recombinant host containing the *Pasteurella*-derived or *Pasteurella*-like synthase gene will serve as an alternative biomaterial with unique properties.

With respect to related microbial GAG synthases other than the HASs, the *E. coli* K5 glycosyltransferases that synthesize heparosan have been identified by genetic and biochemical means. In contrast to the HASs, it appears that two proteins, KfiA and KfiC, are required to transfer the sugars of the disaccharide repeat to the growing polymer chain. The chondroitin-backbone synthesizing enzyme of *E. coli* K4 has been enzymatically characterized, and the gene encoding the relevant glycosyltransferases, KfoC, was recently discovered; it is very homologous (e.g., DNA will cross-hybridize) to the PmCS gene described herein. The KfoC enzyme performs the same reaction as PmCS in vitro, but the former protein appears less robust.

Many *P. multocida* isolates produce GAG or GAG-like molecules as assessed by enzymatic degradation and removal of the capsule of living bacterial cells. Type A *P. multocida*, the major fowl cholera pathogen, makes a capsule that is sensitive to hyaluronidase. Subsequent NMR structural studies of capsular extracts confirmed that HA was the major polysaccharide present. A specific HA-binding protein, aggrecan, also interacts with HA from Type A *P. multocida*. Two other distinct *P. multocida* types, a swine pathogen, Type D, and a minor fowl cholera pathogen, Type F, produce polymers that are chondroitin or chondroitin-like based on the observation that their capsules are degraded by *Flavobacterium* chondroitin AC lyase. After enzymatic removal of the capsule, both types were more readily phagocytosed by neutrophils in vitro. The capsule of Type D cells, but not Type F cells, is also reported to be degraded by heparinase III, suggesting a heparin-type molecule is present, too.

Parent application U.S. Ser. No. 09/842,484 discloses the identification of PmCS (*P. multocida* Chondroitin Synthase), the first chondroitin synthase to be identified and molecularly cloned from any source. Interestingly, a single polypeptide is responsible for the copolymerization of the GlcUA and GalNAc sugars, and thus PmCS is a single protein that is a dual-action transferase that catalyzes the polymerization of UDP-GlcUA and UDP-GalNAc to form chondroitin. The '484 parent application also identified the Type F capsular polymer as an unsulfated chondroitin polymer, and identified organisms with the chondroitin synthase gene (Type F *P. multocida*) as new sources of unsulfated chondroitin polymer.

Certain glycosaminoglycan synthase enzymes (namely enzymes from *Streptococcus*, virus and vertebrates) appear to be self-contained, meaning that they possess both (a) sugar addition or polymerization activity (glycosyltransferase) as well as (b) sugar export functions (transport the polymer across the membrane to the outside of the cell where it can be easily harvested). Certain other distinct enzymes, including those from *Pasteurella*, can catalyze glycosaminoglycan polymerization, but in general are thought to not be able to complete the sugar export step without assistance of other proteins. Gram-negative bacteria have two membranes and are generally thought to need more transport machinery than Gram-positive bacteria with a single membrane. In addition, *Pasteurella* (as well as other sugar-producing Gram-negative pathogens such as *E. coli*) is not a preferred host for the production of glycosaminoglycans intended for use in animals or humans due to the presence of endotoxins or lipopolysaccharides (molecules derived from their outer membrane due to the possibility of inducing shock, etc.

The Gram-negative bacteria capable of GAG biosynthesis, *Escherichia coli* and *Pasteurella multocida*, possess two lipid membranes, and their capsule loci encode many transport-associated proteins in addition to the glycosyltransferases and the UDP-GlcUA forming enzymes (~10-18 kilobases; Roberts, 1996; Townsend et al, 2001). Although many details are not well understood, in the best-studied model, the *E. coli* Group II capsular system, it appears that transport of the nascent polymer chain requires an apparatus composed of at least 7 distinct polypeptide species (Whitfield and Roberts, 1999; Silver et al, 2001). Briefly, a complex containing KpsC, M,S,T assembles on the inner membrane and interacts with the KfiA,B,C catalytic complex. KpsM and T form the ATP-binding cassette (ABC) transporter. A periplasmic protein, KpsD, and a dimer of another inner membrane protein, KpsE, help transport the polymer across the periplasmic space (Arrecubieta, 2001). A porin complex in the outer membrane is recruited to transport the growing polysaccharide chain out of the cell. Certain Kps mutants polymerize the capsular polysaccharide chain, but possess faulty translocation resulting in polymer accumulation in the cytoplasm or periplasm. *P. multocida* is also thought to have a Group II-like transport system based on the sequence similarities and gene arrangement of its putative transport proteins to the *E. coli* proteins.

In the case of PmHAS and PmCS, the carboxyl-terminal tail was thought to contain a docking segment that interacts with the transport mechanism (Jing and DeAngelis, 2000). However, the region(s) of *E. coli* K5 enzymes responsible for docking to the transport apparatus is not known and there is no obviously similar sequence to the carboxyl-terminus of the *Pasteurella* enzymes. Polymer transport across membranes is a difficult phenomenon to study. Therefore, it is thought that any recombinant microbial system endeavoring to utilize the *Pasteurella* glycosaminoglycan synthases must solve or circumvent the transport problem.

Therefore, there is a need felt in the art to provide methods of expressing Gram-negative glycosaminoglycan synthase gene in a Gram-positive bacterial host background to produce GAGs by fermentation in vivo. It is to such methods of expressing a Gram-negative glycosaminoglycan synthase gene in a Gram-positive host that the present invention is directed.

BRIEF DESCRIPTION OF THE SEVERAL VIEWS OF THE DRAWINGS

FIG. 1 illustrates schematics of plasmid Maps utilized in a Chondroitin Synthase Production System for *Bacillus*. Top panel: A cassette with a *Bacillus* ribosome binding site (RBS) and chondroitin synthase gene (PmCS) was cloned into pHCMC04 (pro=xylA Xylose-inducible promoter; con=xylR) and into pHCMC05 (pro=Pspac promoter/IPTG inducible; con=LacI) via the BamHI and SmaI sites of the multiple cloning site. These vectors will replicate in and drug-selected in both *E. coli* (ampicillin with bla) and *B. subtilis* (chloroamphenicol with cat). Bottom panel: In a similar fashion, a cassette with a *Bacillus* ribosome binding site-chondroitin synthase gene (PmCS)-*Bacillus* ribosome binding site-*Bacillus* UDP-GalNAc/UDP-GlcNAc epimerase gene (GalE) was cloned into pHCMC04 (pro=xylA Xylose-inducible promoter; con=xylR) and into pHCMC05 (pro=Pspac promoter/IPTG inducible; con=LacI) via the BamHI and SmaI sites of the multiple cloning site.

Figure 2:
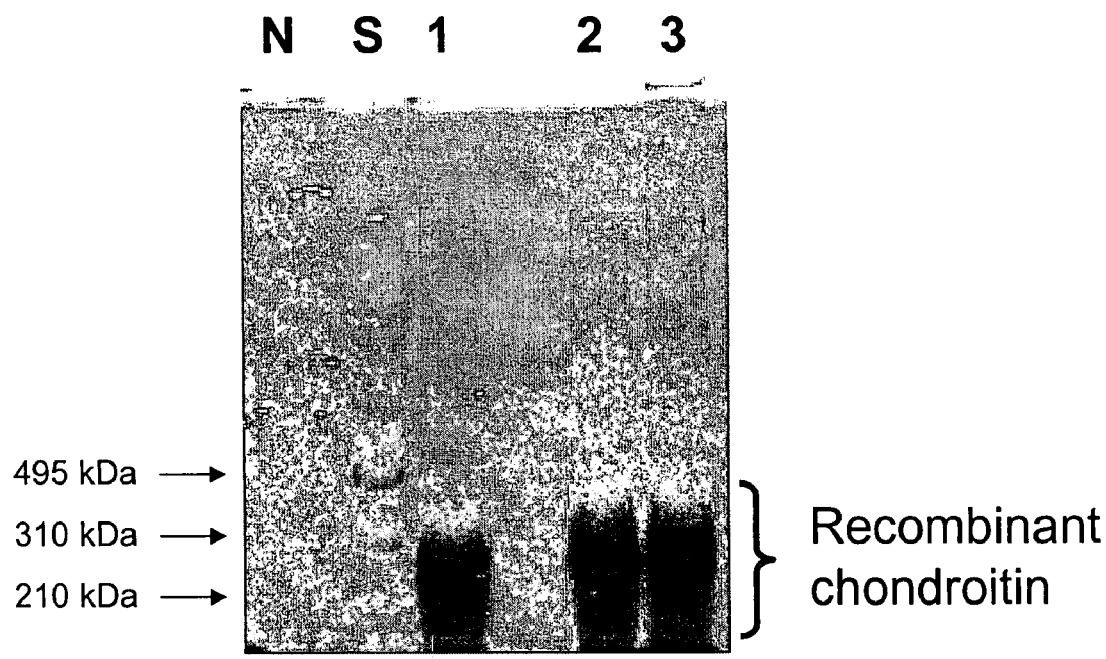

FIG. 2 illustrates an agarose gel analysis of recombinant *Bacillus*-derived Chondroitin. Samples from cultures of *Bacillus subtilis* with vector alone control plasmid (lane N) or containing the PmCS cassette plasmid (lane 1) or the PmCS-GalE cassette plasmid (lanes 2, 3) were run on an agarose gel and stained with StainsAll. The strains with PmCS produce a chondroitin polymer at ~100-300 kDa (based on HA standards, lane S) that is not found in the "no insert" control strain.

Figure 3:
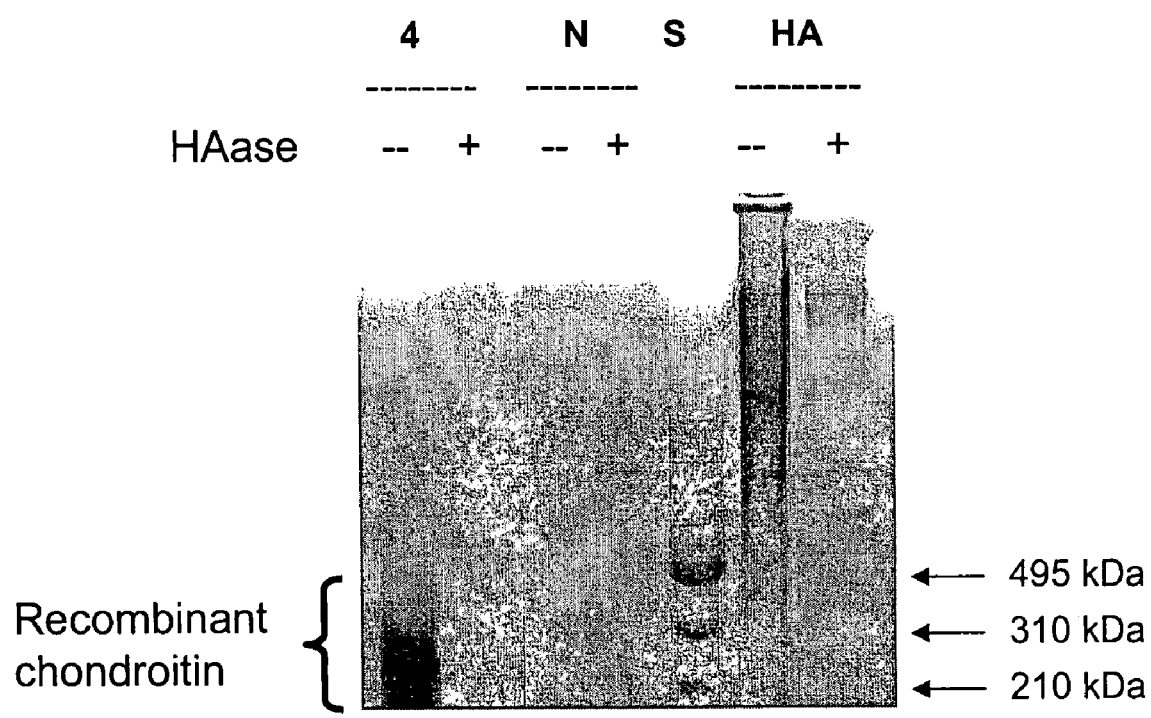

FIG. 3 illustrates agarose gel analysis of recombinant *Bacillus*-derived Chondroitin and the effect of hyaluronidase challenge. Samples from cultures of *Bacillus subtilis* with either a vector alone control plasmid (lane N) or the PmCS-GalE cassette plasmid (lane 4) were prepared. One half of the sample was treated with testicular hyaluronidase (HAase), an enzyme known to cleave both HA and chondroitin polymer to very small chains; the other half of the sample was saved. The HAase treated (+) and untreated (−) samples were then run on an agarose gel and stained with StainsAll. The strains with PmCS gene produce a chondroitin polymer at ~100-300 kDa (based on HA standards, lane S) that is not found in the "no insert" control strain. The polymer is sensitive to enzymatic degradation as is authentic chondroitin.

Figure 4:
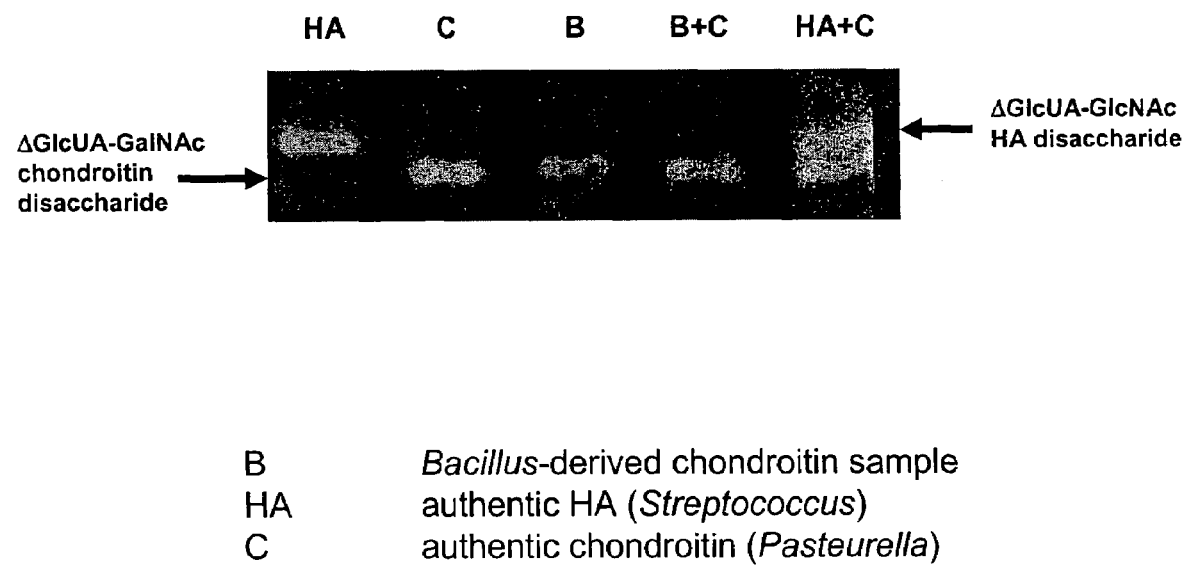

FIG. 4 illustrates Fluorophore-Assisted Carbohydrate Electrophoresis (FACE) gel analysis of recombinant *Bacillus*-derived Chondroitin. A sample from a culture of *Bacillus subtilis* with the PmCS-GalE cassette in the pHCMC05 plasmid (lane B) as well as authentic HA (lane HA) or authentic Chondroitin (lane C) were prepared for FACE by chondroitinase digestion and fluor-tagging of the resulting disaccharides. The samples were then run on a polyacrylamide gel and imaged with UV light. Mixing the recombinant *Bacillus* sample with the authentic chondroitin sample (lane B+C) shows only a single band corresponding to a chondroitin disaccharide (delta-GlcUA-GalNAc) that proves that the strain with PmCS gene produces the authentic chondroitin.

Figure 5:
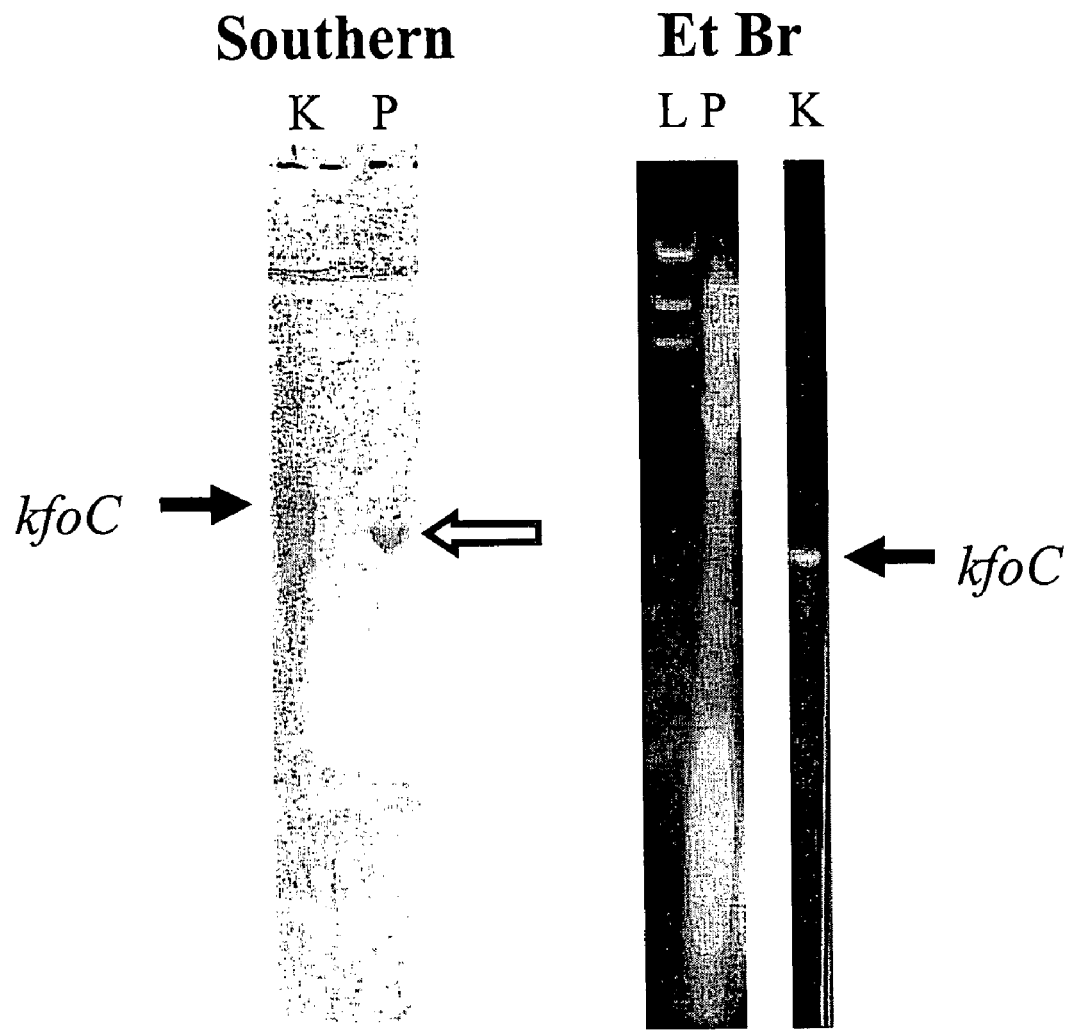

FIG. 5 illustrates a Southern blot showing the hybridization of a chondroitin synthase probe with either *Pasteurella* (denoted as P) or *E. coli* K4 (denoted as K) DNA. The ethidium bromide stained gel shows the total DNA (L is the DNA ladder). Thus, sequences encoding other chondroitin synthase/glycosyltransferases genes similar to PmCS can be identified in other microbial species.

DETAILED DESCRIPTION OF THE INVENTION

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, patent applications, publications, and literature references cited in this specification are hereby expressly incorporated herein by reference in their entirety.

As utilized in accordance with the present disclosure, the following terms, unless otherwise indicated, shall be understood to have the following meanings:

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a Chondroitin Synthase ("CS") coding sequence yet is isolated away from, or purified free from, unrelated genomic DNA, for example, total *Pasteurella multocida* or, for example, mammalian host genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified pmCS (*Pasteurella multocida* Chondroitin Synthase) gene refers to a DNA segment including Chondroitin Synthase coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes genomic sequences, cDNA sequences or combinations thereof. "Isolated substantially away from other coding sequences" means that the gene of interest, in this case pmCS, forms the significant part of the coding region of the DNA segment, and that the DNA segment does not contain large portions of naturally-occurring coding DNA, such as large chromosomal fragments or other functional genes or DNA coding regions. Of course, this refers to the DNA segment as originally isolated, and does not exclude genes or coding regions later added to, or intentionally left in the segment by the hand of man.

Due to certain advantages associated with the use of prokaryotic sources, one will likely realize the most advantages upon isolation of the CS gene from *Pasteurella multocida*. One such advantage is that, typically, eukaryotic enzymes may require significant post-translational modifications that can only be achieved in a eukaryotic host. This will tend to limit the applicability of any eukaryotic CS gene that is obtained. Moreover, those of ordinary skill in the art will likely realize additional advantages in terms of time and ease of genetic manipulation where a prokaryotic enzyme gene is sought to be employed. These additional advantages include (a) the ease of isolation of a prokaryotic gene because of the relatively small size of the genome and, therefore, the reduced amount of screening of the corresponding genomic library and (b) the ease of manipulation because the overall size of the coding region of a prokaryotic gene is significantly smaller due to the absence of introns. Furthermore, if the product of the Chondroitin Synthase gene (i.e., the enzyme) requires posttranslational modifications or cofactors, these would best be achieved in a similar prokaryotic cellular environment (host) from which the gene was derived.

The term "Gram-positive host cell" as used herein will be understood to refer to prokaryotic cells recognized by a Gram staining procedure as Gram-positive. Gram-positive organisms have a cell wall that is relatively thick (approximately 15-80 nm across), and consists of a network of peptidoglycan; this allows the cell wall to retain the basic dye utilized in the Gram stain. Examples of Gram-positive host cells that may be utilized in accordance with the present invention include, but are not limited to, *Bacillus, Staphylococcus, Peptococcus, Lactobacillus, Lactococcus, Actinomyces*, and *Streptomyces* and their allies.

In one embodiment, the Gram-positive host cell is a *Bacillus* cell, such as but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus metaterium, Bacillus pumilus, Bacillus stearothermophilus, Bacillus subtilis* and *Bacillus thuringienisis* cells.

Preferably, DNA sequences in accordance with the present invention will further include genetic control regions which allow the expression of the sequence in a selected recombinant host. Of course, the nature of the control region employed will generally vary depending on the particular use (e.g., cloning host) envisioned.

In particular embodiments, the invention concerns isolated DNA segments and recombinant vectors incorporating DNA sequences which encode a Chondroitin Synthase gene such as but not limited to pmCS. In the case of pmCS, the isolated DNA segments and recombinant vectors incorporating DNA sequences which include within their amino acid sequences an amino acid sequence in accordance with SEQ ID NO:2. Moreover, in other particular embodiments, the invention concerns isolated DNA segments and recombinant vectors incorporating DNA sequences which encode a gene that includes within its amino acid sequence the amino acid sequence of an Chondroitin Synthase gene or DNA, and in particular to an Chondroitin Synthase gene or cDNA, corresponding to *Pasteurella multocida* Chondroitin Synthase—pmCS. For example, where the DNA segment or vector encodes a full length Chondroitin Synthase protein, or is intended for use in expressing the Chondroitin Synthase protein, particular non-limiting examples of sequences are those which are essentially as set forth in SEQ ID NO:1 or 2.

Amino acid segments having chondroitin synthase activity may be isolated by the methods described herein. The term "a sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein, as a gene encoding a sequence essentially as set forth in SEQ ID NO:2, and that is associated with the ability of prokaryotes to produce chondroitin or a "chondroitin like" polymer or a chondroitin synthase polypeptide.

One of ordinary skill in the art would appreciate that a nucleic acid segment encoding enzymatically active chondroitin synthase may contain conservative or semi-conservative substitutions to the sequences set forth in SEQ ID NOS:1 and/or 2 and yet still be within the scope of the invention. For example, a biologically functional equivalent may be an amino acid sequence comprising SEQ ID NO:2 with 0 to 20 conservative amino acid substitutions. Alternatively, a biologically functional equivalent may be an amino acid sequence comprising SEQ ID NO:2 with 0 to 10 conservative amino acid substitutions. As shown in the parent application (U.S. Ser. No. 11/042,530) and in Jing and DeAngelis (Glycobiology, 13:661-671 (2003)), the catalytic residues of PmCS are found in the amino acid residues of the central portion of the open reading frame; thus, truncation or major substitutions of the open reading frame at either termini is also possible while retaining sugar transfer activity.

In particular, the art is replete with examples of practitioner's ability to make structural changes to a nucleic acid segment (i.e., encoding conserved or semi-conserved amino acid substitutions) and still preserve its enzymatic or functional activity. See for example: (1) Risler et al. "Amino Acid Substitutions in Structurally Related Proteins. A Pattern Recognition Approach" J. Mol. Biol. 204:1019-1029 (1988) [". . . according to the observed exchangeability of amino acid side chains, only four groups could be delineated; (i) Ile and Val; (ii) Leu and Met, (iii) Lys, Arg, and Gin, and (iv) Tyr and Phe."]; (2) Niefind et al. "Amino Acid Similarity Coefficients for Protein Modeling and Sequence Alignment Derived from Main-Chain Folding Anoles." J. Mol. Biol. 219:481-497 (1991) [similarity parameters allow amino acid substitutions to be designed]; and (3) Overington et al. "Environment-Specific Amino Acid Substitution Tables: Tertiary Templates and Prediction of Protein Folds," Protein Science 1:216-226 (1992) ["Analysis of the pattern of observed substitutions as a function of local environment shows that there are distinct patterns . . . " Compatible changes can be made.]

These references and countless others available to one of ordinary skill in the art, indicate that given a nucleic acid sequence, one of ordinary skill in the art could make substitutions and changes to the nucleic acid sequence without changing its functionality. Also, a substituted nucleic acid segment may be highly identical and retain its enzymatic activity with regard to its unadulterated parent, and yet still fail to hybridize thereto.

One of ordinary skill in the art would also appreciate that substitutions can be made to the pmCS nucleic acid segment listed in SEQ ID NO:1 without deviating outside the scope and claims of the present invention. Standardized and accepted functionally equivalent amino acid substitutions are presented in Table I.

TABLE I

| Amino Acid Group | Conservative and Semi-Conservative Substitutions |
|---|---|
| NonPolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

The present invention is not limited to the specific chondroitin synthase nucleotide and amino acid sequences disclosed herein. Rather, the present invention also includes chondroitin synthase nucleotide and amino acid sequences from other genus and species that can be identified utilizing the sequences and methods described herein. For example, the use of PmCS sequences described herein allowed for the identification of a homolog, *E. coli* K4 kfoC, by hybridization as described in detail herein after. Such identified sequences also fall within the scope of the present invention, and may be defined in terms of sequence identity to the PmCS sequences or the ability to hybridize to a complement of the pmCS sequences disclosed herein, as described in detail herein after.

Another preferred embodiment of the present invention is a recombinant vector containing (i) a purified nucleic acid segment in accordance with SEQ ID NO:1, or (ii) a purified nucleic acid segment that encodes a protein in accordance with SEQ ID NO:2. As used herein, the term "recombinant vector" refers to a vector that has been modified to contain a nucleic acid segment that encodes a Chondroitin Synthase protein or fragment thereof. The recombinant vector may be further defined as an expression vector comprising a promoter operatively linked to said Chondroitin Synthase encoding nucleic acid segment.

A further preferred embodiment of the present invention is a host cell made recombinant with a recombinant vector comprising a Chondroitin Synthase gene. The preferred recombinant host cell may be a prokaryotic cell. In another embodiment, the recombinant host cell is a eukaryotic cell. As used herein, the term "engineered" or "recombinant" cell is intended to refer to a cell into which a recombinant gene, such as a gene encoding Chondroitin Synthase, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene.

Where one desires to use a host other than *Pasteurella*, as may be used to produce recombinant chondroitin synthase, it may be advantageous to employ a prokaryotic system such as *E. coli, B. subtilis, Lactococcus* sp., or even eukaryotic systems such as yeast or the like. Of course, where this is undertaken it will generally be desirable to bring the chondroitin synthase gene under the control of sequences which are functional in the selected alternative host. The appropriate DNA control sequences, as well as their construction and use, are generally well known in the art as discussed in more detail hereinbelow.

In preferred embodiments, the chondroitin synthase-encoding DNA segments further include DNA sequences, known in the art functionally as origins of replication or "replicons", which allow replication of contiguous sequences by the particular host. Such origins allow the preparation of extrachromosomally localized and replicating chimeric segments or plasmids, to which chondroitin synthase DNA sequences are ligated. In more preferred instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The isolation and use of other replication origins such as the SV40, polyoma or bovine papilloma virus origins, which may be employed for cloning or expression in a number of higher organisms, are well known to those of ordinary skill in the art. In certain embodiments, the invention may thus be defined in terms of a recombinant transformation vector which includes the chondroitin synthase coding gene sequence together with an appropriate replication origin and under the control of selected control regions.

Thus, it will be appreciated by those of skill in the art that other means may be used to obtain the Chondroitin Synthase gene or cDNA, in light of the present disclosure. For example, polymerase chain reaction or RT-PCR produced DNA fragments may be obtained which contain full complements of genes or cDNAs from a number of sources, including other strains of *Pasteurella* or from other bacterial sources, such as libraries. Virtually any molecular cloning approach may be employed for the generation of DNA fragments in accordance with the present invention. Thus, the only limitation generally on the particular method employed for DNA isolation is that the isolated nucleic acids should encode a biologically functional equivalent chondroitin synthase.

Once the DNA has been isolated it is ligated together with a selected vector. Virtually any cloning vector can be employed to realize advantages in accordance with the invention. Typical useful vectors include plasmids and phages for use in prokaryotic organisms and even viral vectors for use in eukaryotic organisms. Examples include pKK223-3, pSA3, recombinant lambda, SV40, polyoma, adenovirus, bovine papilloma virus and retroviruses. However, it is believed that particular advantages will ultimately be realized where vectors capable of replication in both *Lactococcus* or *Bacillus* strains and *E. coli* or *P. multocida* are employed.

Vectors such as these, exemplified by the pSA3 vector of Dao and Ferretti or the pAT19 vector of Trieu-Cuot, et al., allow one to perform clonal colony selection in an easily manipulated host such as *E. coli*, followed by subsequent transfer back into a food grade *Lactococcus* or *Bacillus* strain for production of chondroitin. These are benign and well studied organisms used in the production of certain foods and biotechnology products—otherwise known in the art as GRAS (Generally Regarded As Safe). GRAS organisms are advantageous in that one can augment the *Lactococcus* or *Bacillus* strain's ability to synthesize chondroitin through gene dosaging (i.e., providing extra copies of the HA synthase gene by amplification) and/or the inclusion of additional genes to increase the availability of the chondroitin precursors UDP-GlcUA and UDP-GalNAc. These precursors are made by the action of UDP-glucose dehydrogenase and UDP-GlcNAc/UDP-GalNAc epimerase, respectively. The inherent ability of a bacterium to synthesize chondroitin can also be augmented through the formation of extra copies, or amplification, of the plasmid that carries the chondroitin synthase gene. This amplification can account for up to a 10-fold increase in plasmid copy number and, therefore, the Chondroitin Synthase gene copy number.

Another procedure that would further augment Chondroitin Synthase gene copy number is the insertion of multiple copies of the gene into the plasmid. Another technique would include integrating the Chondroitin Synthase gene into chromosomal DNA. This extra amplification would be especially feasible, since the Chondroitin Synthase gene size is small. In some scenarios, the chromosomal DNA-ligated vector is employed to transfect the host that is selected for clonal screening purposes such as *E. coli* or *Bacillus*, through the use of a vector that is capable of expressing the inserted DNA in the chosen host. In certain instances, especially to confer stability, genes such as the chondroitin synthase gene, may be integrated into the chromosome in various positions in an operative fashion. Unlike plasmids, integrated genes do not need selection pressure for maintenance of the recombinant gene.

In certain other embodiments, the invention concerns isolated DNA segments and recombinant vectors that include within their sequence a nucleic acid sequence essentially as set forth in SEQ ID NO:1. The term "essentially as set forth in SEQ ID NO:1" is used in the same sense as described above and means that the nucleic acid sequence substantially corresponds to a portion of SEQ ID NO:1, and has relatively few codons which are not identical, or functionally equivalent, to the codons of SEQ ID NO:1. The term "functionally equivalent codon" is used herein to refer to codons that encode the same amino acid, such as the six codons for arginine or serine, as set forth in Table I, and also refers to codons that encode biologically equivalent amino acids.

It will also be understood that amino acid and nucleic acid sequences may include additional residues, such as additional N- or C-terminal amino acids or 5' or 3' nucleic acid sequences, and yet still be essentially as set forth in one of the sequences disclosed herein, so long as the sequence meets the criteria set forth above, including the maintenance of biological protein activity where protein expression and enzyme activity is concerned. The addition of terminal sequences particularly applies to nucleic acid sequences which may, for example, include various non-coding sequences flanking either of the 5' or 3' portions of the coding region or may include various internal sequences, which are known to occur within genes.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, such as at least 90 to 95 percent sequence identity, or at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

Allowing for the degeneracy of the genetic code as well as conserved and semi-conserved substitutions, sequences which have between about 40% and about 99%; such as between about 60% and about 90%; or between about 80% and about 99% identity to the nucleotides of SEQ ID NO:1 or the amino acids of SEQ ID NO:2 will be sequences which are "essentially as set forth" in SEQ ID NO:1 or 2. Sequences which are essentially the same as those set forth in SEQ ID NO:1 may also be functionally defined as sequences which are capable of hybridizing to a nucleic acid segment containing the complement of SEQ ID NO:1 under "standard stringent hybridization conditions", "moderately stringent hybridization conditions", "less stringent hybridization conditions", or "low stringency hybridization conditions". Suitable "standard" or "less stringent" hybridization conditions will be well known to those of skill in the art and are clearly set forth hereinbelow. In a preferred embodiment, standard stringent hybridization conditions or less stringent hybridization conditions are utilized.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 60%, and more typically with increasing homologies of at least 70%, 80% and 90%. Two amino acid sequences are homologous if there is a partial or complete identity between their sequences. For example, 60% homology means that 60% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The terms "standard stringent hybridization conditions," "moderately stringent conditions," and "less stringent hybridization conditions" or "low stringency hybridization conditions" are used herein, describe those conditions under which substantially complementary nucleic acid segments will form standard Watson-Crick base-pairing and thus "hybridize" to one another. A number of factors are known that determine the specificity of binding or hybridization, such as pH; temperature; salt concentration; the presence of agents, such as formamide and dimethyl sulfoxide; the length of the segments that are hybridizing; and the like. There are various protocols for standard hybridization experiments. Depending on the relative similarity of the target DNA and the probe or query DNA, then the hybridization is performed under stringent, moderate, or under low or less stringent conditions.

The hybridizing portion of the hybridizing nucleic acids is typically at least about 14 nucleotides in length, and preferably between about 14 and about 100 nucleotides in length. The hybridizing portion of the hybridizing nucleic acid is at least about 60%, e.g., at least about 80% or at least about 90%, identical to a portion or all of a nucleic acid sequence encoding a HAS or chondroitin or heparin synthase or its complement, such as SEQ ID NO:1 or the complement thereof. Hybridization of the oligonucleotide probe to a nucleic acid sample typically is performed under standard or stringent hybridization conditions. Nucleic acid duplex or hybrid stability is expressed as the melting temperature or $T_m$, which is the temperature at which a probe nucleic acid sequence dissociates from a target DNA. This melting temperature is used to define the required stringency conditions. If sequences are to be identified that are related and substantially identical to the probe, rather than identical; then it is useful to first establish the lowest temperature at which only homologous hybridization occurs with a particular concentration of salt (e.g., SSC, SSPE, or HPB). Then, assuming that 1% mismatching results in a 1° C. decrease in the $T_m$, the temperature of the final wash in the hybridization reaction is reduced accordingly (for example, if sequences having >95% identity with the probe are sought, the final wash temperature is decreased by about 5° C.). In practice, the change in $T_m$ can be between about 0.5° C. and about 1.5° C. per 1% mismatch. Examples of standard stringent hybridization conditions include hybridizing at about 68° C. in 5×SSC/5×Denhardt's solution/1.0% SDS, followed with washing in 0.2×SSC/0.1% SDS at room temperature or hybridizing in 1.8×HPB at about 30° C. to about 45° C. followed by washing a 0.2-0.5×HPB at about 45° C. Moderately stringent conditions include hybridizing as described above in 5×SSC\5×Denhardt's solution 1% SDS washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, (Cold Spring Harbor Press, N.Y.); and Ausubel et al. (eds.), 1995, Current Protocols in Molecular Biology, (John Wiley & Sons, N.Y.). Several examples of low stringency protocols include: (A) hybridizing in 5×SSC, 5×Denhardts reagent, 30% formamide at about 30° C. for about 20 hours followed by washing twice in 2×SSC, 0.1% SDS at about 30° C. for about 15 min followed by 0.5×SSC, 0.1% SDS at about 30° C. for about 30 min (FEMS Microbiology Letters, 2000, vol. 193, p. 99-103); (B) hybridizing in 5×SSC at about 45° C. overnight followed by washing with 2×SSC, then by 0.7×SSC at about 55° C. (J. Virological Methods, 1990, vol. 30, p. 141-150); or (C) hybridizing in 1.8×HPB at about 30° C. to about 45° C.; followed by washing in 1×HPB at 23° C.

As is well known in the art, most of the amino acids in a protein are present to form the "scaffolding" or general environment of the protein. The actual working parts responsible for the specific desired catalysis are usually a series of small domains or motifs. Thus a pair of enzymes that possess the same or similar motifs would be expected to possess the same or similar catalytic activity, thus be functionally equivalent. Utility for this hypothetical pair of enzymes may be considered interchangeable unless one member of the pair has a subset of distinct, useful properties. In a similar vein, certain non-critical motifs or domains may be dissected from the original, naturally occurring protein and function will not be affected; removal of non-critical residues does not perturb the important action of the remaining critical motifs or domains. By analogy, with sufficient planning and knowledge, it should be possible to translocate motifs or domains from one enzyme to another polypeptide to confer the new enzyme with desirable characteristics intrinsic to the domain or motif.

Naturally, the present invention also encompasses DNA segments which are complementary, or essentially complementary, to the sequence set forth in SEQ ID NO:1. Nucleic acid sequences which are "complementary" are those which are capable of base-pairing according to the standard Watson-Crick complementarity rules. As used herein, the term "complementary sequence" means a nucleic acid sequence which is substantially complementary, as may be assessed by the same nucleotide comparison set forth above, or as defined as being capable of hybridizing to the nucleic acid segment of SEQ ID NO:1.

The nucleic acid segments of the present invention, regardless of the length of the coding sequence itself, may be combined with other DNA sequences, such as promoters, polyadenylation signals, additional restriction enzyme sites, multiple cloning sites, epitope tags, poly histidine regions, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Naturally, it will also be understood that this invention is not limited to the particular nucleic acid and amino acid sequences of SEQ ID NOS:1 and 2. Recombinant vectors and isolated DNA segments may therefore variously include the Chondroitin Synthase coding regions themselves, coding regions bearing selected alterations or modifications in the basic coding region, or they may encode larger polypeptides which nevertheless include Chondroitin Synthase coding regions or may encode biologically functional equivalent proteins or peptides which have variant amino acids sequences.

The DNA segments of the present invention encompass biologically functional equivalent Chondroitin Synthase proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the Chondroitin Synthase protein or to test Chondroitin Synthase mutants in order to examine chondroitin synthase activity at the molecular level.

Also, specific changes to the Chondroitin Synthase coding sequence can result in the production of chondroitin having a modified size distribution or structural configuration. One of ordinary skill in the art would appreciate that the Chondroitin Synthase coding sequence can be manipulated in a manner to produce an altered chondroitin synthase which in turn is capable of producing chondroitin having differing polymer sizes and/or functional capabilities. For example, the Chondroitin Synthase coding sequence may be altered in such a manner that the chondroitin synthase has an altered sugar substrate specificity so that the chondroitin synthase creates a new chondroitin-like polymer incorporating a different structure via the inclusion of a previously unincorporated sugar or sugar derivative. This newly incorporated sugar could result in a modified chondroitin having different functional properties. As will be appreciated by one of ordinary skill in the art given the Chondroitin Synthase coding sequences, changes and/or substitutions can be made to the Chondroitin Synthase coding sequence such that these desired property and/or size modifications can be accomplished.

Basic knowledge on the substrate binding sites (e.g., the UDP-GlcUA site or UDP-GalNAc site or oligosaccharide acceptor site) of PmCS allows the targeting of residues for mutation to change the catalytic properties of the site. The identity of important catalytic residues of PmCS as well as PmHAS, a close homolog of PmCS, has recently been elucidated (Jing & DeAngelis, Glycobiology, 13: 661-671 (2003); and Jing & DeAngelis, Glycobiology, 10:883-889 (2000)). Appropriate changes at or near these residues would allow other UDP-sugars to bind instead of the authentic chondroitin sugar precursors; thus a new, modified polymer is synthesized. Polymer size changes will be caused by differences in the synthase's catalytic efficiency or changes in the acceptor site affinity. Polymer size changes have been made in the vertebrate HAS, xlHAS1 (DG42), by mutating various residues (see parent application U.S. Ser. No. 11/042,530). As PmCS is a more malleable, robust enzyme than this latter enzyme, similar or superior versions of mutant PmCS which synthesize modified polymers are also possible.

The term "modified structure" as used herein denotes a chondroitin polymer containing a sugar or derivative not normally found in the naturally occurring chondroitin polypeptide. The term "modified size distribution" refers to the synthesis of chondroitin molecules of a size distribution not normally found with the native enzyme; the engineered size could be much smaller or larger than normal.

Various chondroitin products of differing size have application in the areas of drug delivery and the generation of an enzyme of altered structure can be combined with a chondroitin of differing size. Applications in angiogenesis, cancer treatment and wound healing are potentially large if chondroitin polymers of about 10-20 monosaccharides can be made in good quantities. Another particular application for small chondroitin oligosaccharides is in the stabilization of recombinant human proteins used for medical purposes. A major problem with such proteins is their clearance from the blood and a short biological half-life. One present solution to this problem is to couple a small molecule shield that prevents the protein from being cleared from the circulation too rapidly. Very small molecular weight chondroitin is well suited for this role and would be nonimmunogenic and biocompatible. Larger molecular chondroitin attached to a drug or protein may be used to target the reticuloendothelial cell system which has endocytic receptors for chondroitin. Large polymers may be used in high concentrations to make gels or viscous solutions with potential for joint lubrications opthaltmic procedures, and cosmetics.

One of ordinary skill in the art given this disclosure would appreciate that there are several ways in which the size distribution of the chondroitin polymer made by the chondroitin synthase could be regulated to give different sizes. First, the kinetic control of product size can be altered by decreasing temperature, decreasing time of enzyme action and by decreasing the concentration of one or both sugar nucleotide substrates. Decreasing any or all of these variables will give lower amounts and smaller sizes of chondroitin product. The disadvantages of these approaches are that the yield of product will also be decreased and it may be difficult to achieve reproducibility from day to day or batch to batch.

Secondly, the alteration of the intrinsic ability of the enzyme to synthesize a large chondroitin product. Changes to the protein can be engineered by recombinant DNA technology, including substitution, deletion and addition of specific amino acids (or even the introduction of prosthetic groups through metabolic processing). Such changes that result in an intrinsically slower enzyme could then allow more reproducible control of chondroitin size by kinetic means. The final chondroitin size distribution is determined by certain characteristics of the enzyme that rely on particular amino acids in the sequence.

Specific changes in any of these residues can produce a modified hyaluronan or chondroitin that produces a hyaluronan or chondroitin product having a modified size distribution. Engineered changes to seHAS, spHAS, pmHAS, cvHAS and pmCS that decrease the intrinsic size of the hyaluronan or chondroitin polymer that the enzyme can make before the hyaluronan or chondroitin is released will provide powerful means to produce either a hyaluronan or chondroitin polymer product of smaller or potentially larger size than the native enzyme.

Finally, larger molecular weight chondroitin made be degraded with specific chondroitinases to make lower molecular weight chondroitin. This practice, however, is very difficult to achieve reproducibility and one must meticulously repurify the chondroitin to remove the chondroitinases and unwanted digestion products.

Structurally modified chondroitin is no different conceptually than altering the size distribution of the chondroitin product by changing particular amino acids in the desired Chondroitin Synthase and/or more particularly, but not limiting thereto pmCS. Derivatives of UDP-GalNAc, in which the acetyl group is missing from the amide (UDP-GalN) or replaced with another chemically useful group (for example, phenyl to produce UDP-GalNPhe or propyl to produce UDP-GalNPro), is expected to be particularly useful. The free amino group would be available for chemical reactions to derivatize chondroitin in the former case with GalN incorporation. In the latter case, GalNPhe or GalNPro, would make the polymer more hydrophobic or prone to making emulsions. In addition, certain derivatives of GlcUA with extra chemical groups that alter the chemical and/or biological nature of the sugar should be useful. The strong substrate specificity may rely on a particular subset of amino acids among the 10-20% that are conserved. Specific changes to one or more of these residues create a functional chondroitin synthase that interacts less specifically with one or more of the substrates than the native enzyme. This altered enzyme could then utilize alternate natural or special sugar nucleotides to incorporate sugar derivatives designed to allow different chemistries to be employed for the following purposes: (i) covalently coupling specific drugs, proteins, or toxins to the structurally modified chondroitin for general or targeted drug delivery, radiological procedures, etc. (ii) covalently cross linking the hyaluronic acid itself or to other supports to achieve a gel, or other three dimensional biomaterial with stronger physical properties, (iii) covalently linking hyaluronic acid to a surface to create a biocompatible film or monolayer, and (iv) confer resistance to degradation.

In general, prokaryotes are used for the initial cloning of DNA sequences and construction of the vectors useful in the invention. It is believed that a suitable source may be bacterial cells, particularly those derived from strains that can exist on a simple minimal media for ease of purification. Bacteria with a single membrane but a thick cell wall, such as *Staphylococci* and *Streptococci*, are Gram-positive. Gram-negative bacteria such as *E. coli* contain two discrete membranes rather than one surrounding the cell. Gram-negative organisms tend to have thinner cell walls. The single membrane of the Gram-positive organisms is analogous to the inner plasma membrane of Gram-negative bacteria. Additionally, many bacteria possess transport systems that help capsular polymers be secreted from the cell.

In general, plasmid vectors containing origins of replication and control sequences which are derived from species compatible with the host cell are used in connection with these hosts. The vector ordinarily carries an origin of replication, as well as marking sequences which are capable of providing phenotypic selection in transformed cells. An origin of replication may be provided either by construction of the vector to include an exogenous origin or may be provided by the host cell chromosomal replication mechanism. If the vector is integrated into the host cell chromosome, the latter mechanism is often sufficient.

Many promoters have been discovered and utilized, and details concerning their nucleotide sequences have been published, enabling a skilled worker to ligate them functionally with plasmid vectors. Also for use with the present invention one may utilize integration vectors.

In addition to prokaryotes, eukaryotic microbes such as yeast cultures may also be used. *Saccharomyces cerevisiae*, or common baker's yeast is the most commonly used among eukaryotic microorganisms, although a number of other species (e.g., *Pichia*) are commonly available. For expression in *Saccharomyces*, the plasmid YRp7, for example, is commonly used. This plasmid already contains the trp1 gene which provides a selection marker for a mutant strain of yeast lacking the ability to grow without tryptophan, for example, ATCC No. 44076 or PEP4-1. The presence of the trp1 lesion as a characteristic of the yeast host cell genome then provides an effective environment for detecting transformation by growth in the absence of tryptophan. Suitable promoting sequences in yeast vectors include the promoters for the galactose utilization genes, the 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, cytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

Chondroitin sulfate and dermatan sulfate are both derived from the same polymer, i.e. D-glucuronic acid beta (1-3)D-N-acetyl galactosamine beta (1-4). Both chondroitin sulfate and dermatan sulfate can be sulfated at positions 4 or 6 of N-acetyl galactosamine and position 2 of the uronic acid. Neither has been observed to be N-sulfated in nature. The difference between chondroitin sulfate and dermatan sulfate is the epimerisation of glucuronic acid to iduronic acid. There are problems however with the nomenclature and designation of a polysaccharide as either chondroitin sulfate or dermatan sulfate. In particular, the frequency with which iduronic acid must occur rather than glucuronic acid, for the chain to be called a dermatan sulfate chain, is open to interpretation. Thus a chondroitin sulfate chain may have sequences of dermatan sulfate interspersed therein and visa versa. One of ordinary skill in the art would appreciate, however, that a polymer having between 10% and 50% epimerisation of glucuronic acid to iduronic acid would be suitably designated a dermatan sulfate polysaccharide.

A chondroitin polymer is produced by a chondroitin synthase and in particular, but not limited thereto, the pmCS of the present invention. For example, the chondroitin polymer can be converted into a dermatan molecule that may be an even more valuable product than chondroitin itself. The chondroitin polymer can be converted into dermatan either in the purified form or in vivo (i.e. in the host itself). For example, Chang et al. have identified and detailed a reaction of *Azotobacter vinelandii* poly-beta-D-mannuronic acid C-5-epimerase on synthetic D-glucuronans. A dermatan molecule can be made using the *Azotobacter vinelandii* poly-beta-(1->4)-D-mannuronic acid C-5-epimerase to react with a chondroitin polymer made via a chondroitin synthase such as pmCS. (Chang et al. *Action of Azotobacter vinelandii poly-beta-D-mannuronic Acid C-5-epimerase on Synthetic D-Glucuronans*, Carbohydrate Research, Dec. 1, 2000; 329(4):913-22, which is expressly incorporated herein in its entirety by reference). U.S. Pat. No. 5,939,289 issued to Ertesvag et al., which is expressly incorporated herein by reference, also discloses a C-5 epimerase which may be used to convert the chondroitin molecule produced by the *P. multocida* chondroitin synthase into an unsulfated dermatan molecule. The C-5 epimerase is expected to work on the chondroitin polymer as the Chang et al. paper describes epimerization of a variety of polysaccharides containing uronic acids including oxidized starch and chitin.

Alternatively, instead of step-wise chondroitin synthesis followed by epimerization reaction, an in vivo combined method should be possible. This is very suitable in pmCS/*Azotobacter* epimerase case as the reactions are compatible and both genes are from Gram-negative bacteria. Both enzymes have been shown to function in *E. coli*. Placing both genes in one cell and allowing contact of chondroitin and the epimerase results in the desired product.

Further, an assay procedure for measuring the reactions catalyzed by polyuronic acid C-5 epimerases can be used. (See e.g., Chang et al. *Measurement of the Activity of Polyuronic Acid C-5 Epimerases*, Anal. Biochem., Apr. 10, 1998; 258(1):59-62, which is expressly incorporated herein in its entirety by reference) Action of C-5 epimerases inverts the C-6 carboxyl group of polyuronic acids thus converting beta-linked residues into alpha-linked residues or vice versa. The above-identified assay takes advantage of the greater susceptibility of the acid hydrolysis of alpha-glycosidic linkages than beta-glycosidic linkages. Thus, acid treatment of experimental polymers (the product) results in a color yield but the parent starting material does not result in a substantial color yield. The method of this particular assay involves the partial acid hydrolysis of the polyuronic acid before and after reaction with the C-5 epimerase. The greater or lesser amounts of uronic acid released (solubilized) before and after reaction of the C-5 epimerase are a measure of the amount of alpha- or beta-glycosidic linkages that are formed and a measure of the amount of catalysis by the enzyme. In this manner, the conversion chondroitin polymer to dermatan can be catalyzed and monitored for reaction and efficiency.

The chondroitin molecule made by the PmCS enzyme is an ideal polymeric starting material for the creation of a dermatan sulfate molecule. Certain mammalian epimerases only epimerize unsulfated polymer molecules. For example, the C-5 uronosyl epimerase, which is capable of converting a chondroitin molecule into a dermatan molecule, will only epimerize an unsulfated chondroitin molecule. Unsulfated chondroitin molecules are not found in nature, and chondroitin sulfate must be either desulfated or an unsulfated chondroitin molecule must be recombinantly produced. Since no chondroitin synthase has been known prior to or since the discovery of the pmCS enzyme, one of ordinary skill in the art would have to expend additional time, money, and capital in order to convert sulfated chondroitin into unsulfated or desulfated chondroitin. Once the chondroitin is unsulfated, the mammalian epimerases can be used to convert the chondroitin molecule into a dermatan molecule. By utilizing a chondroitin synthase, such as pmCS, one of ordinary skill in the art is capable of producing an unsulfated chondroitin molecule which is an ideal starting material for epimerization by a mammalian epimerase. For one such mammalian epimerase and methods of using same, see e.g. Malmstrom A., *Biosynthesis of Dermatan Sulfate—Substrate Specificity of the C-5 Uronosyl Epimerase*, J. Biol. Chem., Jan. 10, 1984; 259(1): 161-5, which is expressly incorporated herein by reference in its entirety.

Utilizing enzymatic sulfation, the chondroitin polymer—turned—dermatan molecule can be sulfated, thereby creating an even more valuable and flexible polymer for anticoagulation, device coatings, and/or other biomaterial. As pointed out in the Eklund et al. article entitled *Dermatan is a Better Substrate for 4-O-sulfation than Chondroitin: Implications in the Generation of 4-O-sulfated, L-iduronic-rich Galactosaminoglycans*, Arch. Biochem. Biophys., Nov. 15, 2000; 383(2):171-7, which is expressly incorporated in its entirety herein by reference, dermatan is not only more easily enzymatically sulfated than chondroitin, but sulfated dermatan is a more valuable, flexible and useful product than chondroitin. Thus, utilizing a chondroitin synthase such as pmCS, one or ordinary skill in the art, given the present disclosure, would be able to produce natural and non-natural chondroitin as well as dermatan and dermatan sulfate. Other articles, which are expressly incorporated herein in their entirety by reference, outline other methodologies for enzymatically sulfating dermatan. Bhakta et al. *Sulfation of N-acetylglucosamine by Chondroitin 6-Sulfotransferase 2 (GST-5)*, J. Biol. Chem., Dec. 22, 2000; 275(51):40226-34; Ito et al. *Purification and Characterization of N-acetylgalactosamine 4-sulfate 6-O-Sulfotransferase from the Squid Cartilage*, J. Biol. Chem., Nov. 3, 2000; 275(44):34728-36.

In addition to enzymatic sulfation, the dermatan polymer can be chemically sulfated. One method for chemical sulfation is outlined in the article by Garg et al. entitled *Effect of Fully Sulfated Glycosaminoglycans on Pulmonary Artery Smooth Muscle Cell Proliferation*, Arch. Biochem. Biophys., Nov. 15, 1999; 371(2): 228-33, which is expressly incorporated herein in its entirety by reference. Typically, the polysaccharide in an anhydrous solvent is treated with sulfur trioxide or chlorosulfonic acid. In any event, one of ordinary skill in the art given the chondroitin synthase (PmCS) of the present invention and the methodology for producing a chondroitin polymer from the PmCS enzyme would be capable of using the epimerization reaction to form a dermatan molecule and then sulfating this dermatan molecule by known enzymatic, or chemical sulfation techniques. Alternatively, unepimerized chondroitin could be sulfated by any means as well.

Also, U.S. Pat. No. 4,990,601 issued to Skjak-Braek et al., which is expressly incorporated herein by reference in its entirety, discloses a chemical process using supercritical $CO_2$ which epimerizes uronic acid in a compound. Utilizing a chondroitin polypeptide using the pmCS of the present invention and the $CO_2$ epimerization method of Skjak-Braek et al., one of ordinary skill in the art can easily make unsulfated dermatan molecules.

An Example is provided hereinbelow. However, the present invention is to be understood to not be limited in its application to the specific experimentation, results and laboratory procedures. Rather, the Example is simply provided as one of various embodiments and is meant to be exemplary, not exhaustive.

EXAMPLE

Materials and Methods

Materials and *Pasteurella* Strains—Unless otherwise noted, all chemicals were from Sigma or Fisher, and all molecular biology reagents were from Promega. The wild-type encapsulated Type F *P. multocida* strains, P-4679 and P-3695, were obtained from Dr. Richard Rimler (USDA, Ames, Iowa). These strains were isolated from turkeys with fowl cholera. P-4679 had a slightly larger capsule than P-3695 as judged by light microscopy and India Ink staining.

Isolation of Capsule Biosynthesis Locus DNA—A lambda library of Sau3A partially digested P-4679 DNA (4-9 kb average length insert) was made using the BamHI-cleaved Zap Express™ vector system (Stratagene). The plaque lifts were screened by hybridization (5×SSC, 50° C.; 16 hrs) with the digoxigenin-labeled probe using the manufacturer guidelines for colorimetric development. *E. coli* XLI-Blue MRF' was co-infected with the purified, individual positive lambda clones and ExAssist helper phage to yield phagemids. The resulting phagemids were transfected into *E. coli* XLOLR cells to recover the plasmids. Sequence analysis of the plasmids revealed a novel open reading frame (ORF), i.e., PmCS (DeAngelis and Padgett-McCue, 200, *J. Biol. Chem.*). The central portion of both the PmCS and the PmHAS polypeptides (residues 430-530) is most homologous to bacterial glycosyltransferases from a wide variety of genera, including *Streptococcus, Vibrio, Neisseria* and *Staphylococcus*, which form exopolysaccharides or the carbohydrate portions of lipopolysaccharides. Some of the most notable sequence similarities are the DGSTD and the DxDD motifs. Directly downstream of the pmCS gene a putative UDP-glucose dehydrogenase gene was identified. Therefore, the relative gene order [KfaA homolog—polysaccharide synthase gene—UDP-glucose dehydrogenase gene] in this portion of the *Pasteurella* Type F capsule operon is the same as that found in *Pasteurella* Type A.

Construction and Expression of Recombinant *P. multocida* Chondroitin Synthase in *Bacillus* (FIG. 1). Construction of suitable vectors containing the desired coding and control sequences employ standard ligation and transformation techniques. Isolated plasmids or DNA fragments are cleaved, tailored, and religated in the form desired to construct the plasmids required. The PmCS ORF (SEQ ID NO:1; encoding residues 1-965 of SEQ ID NO:2) in the insert of one of the excised lambda clones, pPmF4A (DeAngelis and Padgett-McCue, 200, *J. Biol. Chem.*), was amplified by polymerase chain reaction (PCR) with Taq or Pfu DNA polymerase. The sense primer corresponded to the sequence at the deduced amino terminus of the ORF preceded by a *Bacillus* ribosome binding sequence (RBS) and a unique restriction site compatible with the expression plasmid. The antisense primer encoded the carboxyl terminus of the ORF followed by a stop codon and a second (i.e., different from the sense primer site) unique restriction site compatible with the expression plasmids. The new restriction sites were used to facilitate the cloning of the open reading frame downstream of the transcriptional promoter of the vector. The resulting PCR product encoding the RBS/synthase gene cassette was purified and concentrated using GeneClean. The insert cassette was cleaved at the two flanking unique restriction sites (sites added with the two PCR primers above) and cloned into the two different plasmid-based expression vectors, pHCMC04 and pHCMC05 (*Bacillus* Genetic Stock Center), cut with the restriction enzymes to generate compatible ends suitable for ligation. These expression vectors have been constructed allowing stable intracellular expression of recombinant proteins in *Bacillus subtilis* strains (Nguyen H G et al., *Plasmid*, 54:241-8 (2005)). These expression vectors are based on the recently described *Escherichia coli*-*B. subtilis* shuttle vector pMTLBS72 which replicates as theta circles. Two different controllable promoters are used on pHCMC04 and pHCMC05: P(xylA) and P(spac), respectively, which respond to the addition of xylose and IPTG, respectively. The ligated products (FIG. 1; top panel) were transformed into *E. coli* and plated on LB with ampicillin (100 μg/ml). In addition to the PmCS gene alone, a second series of constructs with the GalE gene (UDP-GlcNAc/GalNAc epimerase to help increase flux of UDP-GalNAc production; amplified by PCR from *Bacillus subtilis* genomic DNA with suitable primers and Pfu polymerase) was also created (FIG. 1; bottom panel).

Colonies were analyzed by restriction digestion and DNA sequencing. Clones containing a plasmid with the desired ORF were transformed into *Bacillus subtilis* 168 (*Bacillus* Genetic Stock Center), the production/expression host, and maintained on LB media with chloramphenicol (5 μg/ml) at 30° C. Log phase cultures in defined synthetic media (e.g., Spizzens) were induced with beta-isopropylthiogalactoside (0.1-0.5 mM final) or xylose (0.1-0.5% final). The cells were removed by centrifugation, and the chondroitin was purified by the CPC method (below) and tested.

Purification of Chondroitin—The anionic polymer in cultures of the recombinant *Bacillus* bacteria was purified by cetylpyridinium chloride (CPC) precipitation. Cells were grown in complete defined media (150 ml) with drug selection with mild shaking overnight at 37° C. Cells were removed by centrifugation (3,000×g, 10 min), and spent culture media was harvested. GAGs in the aqueous extract were precipitated by the addition of cetylpyridinium chloride (1% w/v final concentration). After standing for 10 min, the precipitate was collected by high-speed centrifugation and redissolved in 2.5 M NaCl. The mixture was clarified by high-speed centrifugation and the supernatant was precipitated with 3 vol of ethanol. The precipitate was washed with 70% ethanol, dried slightly, and resuspended in 2.5 M NaCl. The ethanol precipitation procedure was repeated, and the pellet was redissolved in water. Another round of ethanol precipitation (2 vol.) was performed. The final pellet was dissolved in water.

Size Analysis and Enzymatic Degradation of Polymers (FIGS. 2 and 3). Gel electrophoresis was used to analyze the size distribution of the recombinant polymers. Polymers were analyzed using 1 to 1.2% 1×TAE agarose gels (30 V, 5 h, Stains-All detection (Lee and Cowman, 1994) (FIG. 2). The testicular hyaluronidase from Sigma (St. Louis, Mo.) was employed to destroy and thus identify HA or chondroitin chains (note: this enzyme will digest both HA and chondroitin) (FIG. 3). Defined HA molecular weight standards were from Hyalose L. L. C. (Oklahoma City, Okla.). Kilobase DNA standards were from Stratagene (La Jolla, Calif.).

Disaccharide Analysis—The FACE (fluorophore-assisted carbohydrate electrophoresis) method was used to identify the sugar repeats of the GAGs produced (FIG. 4). In general, a sample (25 μg) was dissolved in 100 μl 0.1 M ammonium acetate, pH 7.0 and 1 μl Chondroitinase ABC (16.6 mU/μl; Sigma) was added followed by incubation at 37° C. (4 hrs to overnight). The sample was then lyophilized and re-dissolved in 40 μl 2-aminoacridone HCl (12.5 mM dissolved in 85/15 dimethyl sulfoxide (DMSO)/acetic acid and incubated for 15 min in the dark at room temperature. Then 40 μl 1.25M sodium cyanoborohydride in water was added followed by incubation at 37° C. The sample was lyophilized and re-dissolved before running the polyacrylamide gel in Tris borate buffer (Glycobiology, Vol. 13(1): 1G-3G, 2003). Approximately 0.5 micrograms of sample/lane were run on the gel. Bands were detected by fluorescence with ultraviolet light.

Detection of PmCS gene homologs. The pmCS gene DNA was used as a hybridization probe for detecting the *E. coli* K4 kfoC gene DNA (FIG. 5). Basically, a commercial Southern blot kit (Dig Hi-Prime, Roche) was used to label restriction fragments containing pmCS with digoxigenin probe. This probe was used to analyze a Southern blot containing a PstI/EcoRI digest of Type F *Pasteurella multocida* genomic DNA (a positive control; P lane), a PCR product of the kfoC gene (corresponding to product of Ninomiya et al., 2002; lane K), or Lambda HindIII standard (lane L). The hybridization was carried out at 37° C. overnight in the manufacturer's buffer (Dig Easy Hyb). The blot was washed with 2×SSC, 0.1% SDS at 30° C. for 15 min twice, then for 30 min in 0.5×SSC, 0.1% SDS at 30° C. before using the manufacturer's Dig-antibody protocol for colorimetric detection. The kfoC band is apparent (KfoC black arrow) as well as the native *Pasteurella* gene (white arrow). No spurious hybridization signals were seen from other irrelevant DNA species. Therefore, the knowledge of the pmCS sequence can be used to identify other chondroitin synthase candidates for various uses (e.g., fermentation in vivo, production in vitro) by known standard methodology.

Results/Discussion

Heterologous Expression of a Functional *P. multocida* Chondroitin Synthase—Previously, Western blot analysis using a monospecific antipeptide antibody was used to detect the production of pmCS$^{1-704}$ or pmHAS$^{1-703}$ polypeptide made in *E. coli* (see FIG. 2 of parent application U.S. Ser. No. 11/042,530). Both enzymes contain a sequence that corresponds exactly to the synthetic peptide used to generate the antibody. Extracts derived from *E. coli* cells containing the pmCS$^{1-704}$ plasmid contained an immunoreactive band of the appropriate size (i.e. predicted to be 80 kDa), but this band was not present in samples from cells with the vector alone control. Extracts derived from *E. coli* cells containing the pmCS$^{1-704}$ plasmid, but not samples from cells with the vector alone, synthesized chondroitin polymer in vitro when supplied with both UDP-GlcUA and UDP-GalNAc simultaneously (see Table 3 of U.S. Ser. No. 11/042,530).

The present invention demonstrates production of a chondroitin polymer by recombinant *Bacillus* possessing a pmCS gene (borne by a plasmid such as in FIG. 1) in vivo. The high molecular weight polymer in the spent culture media was detected by agarose gel electrophoresis (0.8% gel run in 1×TAE system) (FIGS. 2 and 3). With StainsAll staining, HA and native *P. multocida* Type F polymer (=unsulfated chondroitin) or recombinant *Bacillus*-derived polymer all stain blue. The recombinant polymer was sensitive to an enzyme treatment (FIG. 3) in a similar fashion to authentic chondroitin. Any functional microbial chondroitin synthase should behave in a similar fashion to PmCS in a recombinant in vivo system, especially if the two sequences are homologous or the catalysts possess similar reaction mechanisms. It is also expected that the location of the pmCS gene, either on a plasmid or integrated into the chromosome or present in a phage, is expected to be functional in the recombinant Gram-positive bacterial in vivo system as well.

The native and the recombinant chondroitin polymer are smaller than HA produced by bacterial fermentation (FIG. 3), but still form very large chains of about 100 kDa to about 300 kDa. All other non-PmCS-derived chondroitin reported in the literature has a size below 100 kDa. Such higher molecular weight polymers will have increased viscosity that is more useful for certain medical devices and viscoelastic supplements. The polymer purified from recombinant cultures is a suitable starting material for further processing (e.g., cleavage, cross-linking, sulfation, epimerization) into various therapeutics (e.g., biomaterials, nutraceuticals, or anticoagulants).

Compositional Analysis of Chondroitin Synthase-derived Polymers. Previous work by others has shown that the Type F capsule is removed from bacterial cells by treatment with chondroitin AC lyase. It was found that a fragment of the specific HA-binding protein, aggrecan, in the HA-TEST assay (Pharmacia) did not cross-react with extracts of the Type F polymer, but readily detected the HA in parallel extracts from Type A bacteria. Acid hydrolysis and monosaccharide analysis of the Type F polymer showed that it contained the sugars galactosamine and GlcUA (Table 2 and FIG. 5 of U.S. Ser. No. 11/042,530). The NMR spectrum and other analyses of Type F polymer were also consistent with the unsulfated chondroitin structure (DeAngelis et al, 2002, Carb. Research Vol 337:p. 1547-1522).

In general, it may be difficult to distinguish HA and unsulfated chondroitin; these isomers only differ in the C4 position of their hexosamine sugars. Experimental methods such as mass spectrometry alone, simple chemical assays, or many electrophoretic methods are not sufficient. However, FACE, a specialized electrophoretic method, is very useful for deciphering GAG disaccharide composition. Indeed, different sugar isomers are readily distinguished, and this method is accepted as a 'gold standard' in glycobiology for many types of glycans (e.g. moieties from N- or O-glycoproteins) and monosaccharides (e.g. can separate isobaric, isomeric sugars such as glucose, galactose, and mannose). In this invention, the FACE profile of the recombinant *Bacillus*-derived chondroitin digest was indistinguishable from the authentic unsulfated chondroitin (i.e. native Type F *Pasteurella* digest) (FIG. 4); the mixing experiments further demonstrated that the component peaks migrated identically. The chondroitin (both native and recombinant) digests were easily distinguished from the HA digest, thus demonstrating the power of FACE analysis.

Models of Production of GAGs with a Gram-negative GAG Synthase in a Gram-positive Bacterial Host. The PmHAS protein was hypothesized to interact with a putative polysaccharide transporter system or a membrane-bound partner via its carboxyl terminus, because deletion of residues 704 to 972 from the native-length enzyme resulted in the formation of a soluble enzyme (Jing and DeAngelis, 2000). However, no substantial membrane-associated or hydrophobic regions are predicted to reside in this sequence. As PmHAS and PmCS are highly homologous in this region, which is not essential for their glycosyltransferase activities, it was suggested that the carboxyl terminus contains domains or motifs required for interacting with the polysaccharide transport machinery or a membrane-bound partner in vivo.

Several hypotheses for production of a GAG by a Gram-negative *Pasteurella* synthase in a Gram-positive host are possible, including: a) the synthase docks and uses Gram-positive polymer transport machinery, or b) the synthase can facilitate its own transport across a single inner membrane. Empirically, the Gram-positive host, and more specifically a *Bacillus* host, can support GAG production of a *Pasteurella* GAG synthase; this finding is neither expected nor predicted, but clearly of utility to facilitate GAG manufacture in a defined, GRAS (generally regarded as safe), endotoxin-free fermentation system.

Some Gram-negative bacteria (e.g., *E. coli*) and some Gram-positive bacteria (*B. subtilis*) possess an UDP-GlcNAc/UDP-GalNAc epimerase (GalE). Therefore, the hexosamine precursor for chondroitin is available for polysaccharide biosynthesis without the need to gain an auxiliary metabolic enzyme simultaneously, but adding an extra gene to alter the pool size of any required UDP-sugar is predicted to be favorable. In constructs using an auxiliary GalE gene behind the pmCS gene (FIG. 1, bottom) in *Bacillus*, the chondroitin yield is increased (FIG. 2); the most likely explanation is that with more epimerase protein (derived from both chromosomal and man-made plasmid-derived genes, rather than just the original native state of one chromosomal endogenous GalE), the flux of GalNAc into the chondroitin polymer is increased.

Typically the UDP-glucose dehydrogenase, the enzyme that forms the UDP-GlcUA precursor, is found in Gram-negative bacteria only if the microbe possesses a GlcUA-containing polymer or glycoconjugate. In both Type A and Type F *P. multocida*, the UDP-glucose dehydrogenase gene is directly downstream of the GAG synthase. Some Gram-positive bacteria (*B. subtilis*) also possess UDP-glucose dehydrogenase. But again boosting the level of any UDP-sugar by adding an extra gene to alter the pool size of any UDP-sugar is predicted to be favorable. This enhancement was shown to be favorable with HA production in *B. subtilis* (Widner et al., Appl. Environ. Microbiol., 71: 3747-3752 (2005)). In addition, the elimination of competing (e.g. sinks for UDP-sugars) or undesirable (e.g., contaminant or detrimental molecule biosynthesis) pathways are also expected to facilitate production of the target chondroitin polymers.

Thus, it should be apparent that there has been provided in accordance with the present invention, methods of expressing a Gram-negative glycosaminoglycan synthase gene in a Gram-positive host and production of a glycosaminoglycan utilizing same, that fully satisfies the objectives and advantages set forth above. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

What is claimed is:

1. A method for producing a chondroitin polymer in vivo, comprising the steps of:

providing a purified nucleic acid segment encoding an enzymatically active chondroitin synthase, wherein the chondroitin synthase is a single protein that is a dual-action transferase that catalyzes the polymerization of UDP-GlcUA and UDP-GalNAc to form chondroitin, and wherein the purified nucleic acid segment comprises at least one of:

(A) the nucleic acid sequence of SEQ ID NO:1;
(B) a nucleic acid sequence encoding the amino acid sequence of SEQ ID NO:2;
(C) a nucleic acid sequence that is at least 80% identical to SEQ ID NO:1; and
(D) a nucleic acid sequence that encodes an amino acid sequence that is at least 90% identical to the entirety of SEQ ID NO:2;

providing a Gram-positive host cell;

placing the purified nucleic acid segment encoding the enzymatically active chondroitin synthase in the Gram-positive host cell, thereby providing a recombinant Gram-positive host cell having a purified nucleic acid segment encoding an enzymatically active chondroitin synthase therein;

placing the recombinant Gram-positive host cell in a medium suitable for the expression of the enzymatically active chondroitin synthase, whereby a chondroitin polymer is produced; and isolating the chondroitin polymer.

2. The method of claim 1 wherein, in the step of providing a purified nucleic acid segment encoding an enzymatically active chondroitin synthase, the purified nucleic acid segment comprises (A).

3. The method of claim 1 wherein, in the step of providing a purified nucleic acid segment encoding an enzymatically active chondroitin synthase, the purified nucleic acid segment comprises (B).

4. The method of claim 1 wherein, in the step of providing a purified nucleic acid segment encoding an enzymatically active chondroitin synthase, the purified nucleic acid segment comprises (C).

5. The method of claim 1 wherein, in the step of providing a purified nucleic acid segment encoding an enzymatically active chondroitin synthase, the purified nucleic acid segment comprises (D).

6. The method of claim 1 wherein, in the step of providing a Gram-positive host cell, the Gram-positive host cell is selected from the group consisting of a *Bacillus* cell, *Staphylococcus* cell, *Peptococcus* cell, *Lactobacillus* cell, *Lactococcus* cell, *Actinomyces* cell, and *Streptomyces* cell.

7. The method of claim 1 wherein, in the step of providing a Gram-positive host cell, the Gram-positive host cell comprises nucleic acid segments encoding enzymes which produce UDP-GlcUA and UDP-GalNAc.

8. The method of claim 1 wherein, in the step of isolating the chondroitin polymer, the chondroitin polymer is isolated from at least one of the medium and the recombinant Gram-positive host cell.

9. The method of claim 8, further comprising the step of purifying the isolated chondroitin polymer.

10. The method of claim 1, further comprising the step of sulfating the isolated chondroitin polymer.

11. The method of claim 1, further comprising the step of epimerizing the isolated chondroitin polymer.

12. A method for producing a chondroitin polymer in vivo, comprising the steps of:
providing a purified nucleic acid segment encoding an enzymatically active chondroitin synthase, wherein the chondroitin synthase is a single protein that is a dual-action transferase that catalyzes the polymerization of UDP-GlcUA and UDP-GalNAc to form chondroitin, and wherein the purified nucleic acid segment comprises at least one of:
(A) the nucleic acid sequence of SEQ ID NO:1;
(B) a nucleic acid sequence encoding the amino acid sequence of SEQ ID NO:2;
(C) a nucleic acid sequence that is at least 80o/a identical to SEQ ID NO:1; and
(D) a nucleic acid sequence that encodes an amino acid sequence that is at least 90o/a identical to the entirety of SEQ ID NO:2;
providing a *Bacillus* host cell, wherein the *Bacillus* host cell comprises nucleic acid segments encoding enzymes which produce UDP-GlcUA and UDP-GalNAc;
placing the purified nucleic acid segment encoding the enzymatically active chondroitin synthase in the *Bacillus* host cell, thereby providing a recombinant *Bacillus* host cell having a purified nucleic acid segment encoding an enzymatically active chondroitin synthase therein;
placing the recombinant *Bacillus* host cell in a medium suitable for the expression of the enzymatically active chondroitin synthase, whereby a chondroitin polymer is produced; and
isolating the chondroitin polymer.

13. The method of claim 12 wherein, in the step of providing a purified nucleic acid segment encoding an enzymatically active chondroitin synthase, the purified nucleic acid segment comprises (A).

14. The method of claim 12 wherein, in the step of providing a purified nucleic acid segment encoding an enzymatically active chondroitin synthase, the purified nucleic acid segment comprises (B).

15. The method of claim 12 wherein, in the step of providing a purified nucleic acid segment encoding an enzymatically active chondroitin synthase, the purified nucleic acid segment comprises (C).

16. The method of claim 12 wherein, in the step of providing a purified nucleic acid segment encoding an enzymatically active chondroitin synthase, the purified nucleic acid segment comprises (D).

17. The method of claim 12, further comprising the step of purifying the isolated chondroitin polymer.

18. The method of claim 12, further comprising the step of sulfating the isolated chondroitin polymer.

19. The method of claim 12, further comprising the step of epimerizing the isolated chondroitin polymer.

* * * * *

UNITED STATES PATENT AND TRADEMARK OFFICE
CERTIFICATE OF CORRECTION

PATENT NO. : 7,642,071 B2 Page 1 of 1
APPLICATION NO. : 11/701262
DATED : January 5, 2010
INVENTOR(S) : Paul L. DeAngelis It is certified that error appears in the above-identified patent and that said Letters Patent is hereby corrected as shown below:

Column 2, line 21: Delete "GIcUA" and replace with -- GlcUA --

In the Claims:
Column 31, line 60: Delete "UDP-GIcUA" and replace with -- UDP-GlcUA --

Column 31, line 60: Delete "UDP-GaINAc" and replace with -- UDP-GalNAc --

Column 33, line 25: Delete "UDP-GIcUA" and replace with -- UDP-GlcUA --

Column 33, line 25: Delete "UDP-GaINAc." and replace with -- UDP-GalNAc. --

Column 33, line 42: Delete "UDP-GIcUA" and replace with -- UDP-GlcUA --

Column 33, line 42: Delete "UDP-GaINAc" and replace with -- UDP-GalNAc --

Column 34, line 4: Delete "800/a" and replace with -- 80% --

Column 34, line 7: Delete "900/a" and replace with -- 90% --

IN THE SPECIFICATION:

On Column 2, line 43; Replace "Fig. (d)" with -Fig. 1(d)--.

Column 34, line 11: Delete "UDP-GIcUA" and replace with -- UDP-GlcUA --

Column 34, line 11: Delete "UDP-GaINAc;" and replace with -- UDP-GalNAc; --

Signed and Sealed this

Twentieth Day of July, 2010

David J. Kappos
*Director of the United States Patent and Trademark Office*

UNITED STATES PATENT AND TRADEMARK OFFICE
CERTIFICATE OF CORRECTION

PATENT NO. : 7,642,071 B2
APPLICATION NO. : 11/701262
DATED : January 5, 2010
INVENTOR(S) : Paul L. DeAngelis It is certified that error appears in the above-identified patent and that said Letters Patent is hereby corrected as shown below:

Column 2, line 43; Replace "FIG. (d)" with -- Fig. 1(d) --

Signed and Sealed this
Twenty-eighth Day of December, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,642,071 B2 | Page 1 of 1 |
| APPLICATION NO. | : 11/701262 | |
| DATED | : January 5, 2010 | |
| INVENTOR(S) | : Paul L. DeAngelis | |

It is certified that error appears in the above-identified patent and that said Letters Patent is hereby corrected as shown below:

Column 2, line 21: Delete "GIcUA" and replace with -- GlcUA --

In the Claims:
Column 31, line 60: Delete "UDP-GIcUA" and replace with -- UDP-GlcUA --

Column 31, line 60: Delete "UDP-GaINAc" and replace with -- UDP-GalNAc --

Column 33, line 25: Delete "UDP-GIcUA" and replace with -- UDP-GlcUA --

Column 33, line 25: Delete "UDP-GaINAc." and replace with -- UDP-GalNAc. --

Column 33, line 42: Delete "UDP-GIcUA" and replace with -- UDP-GlcUA --

Column 33, line 42: Delete "UDP-GaINAc" and replace with -- UDP-GalNAc --

Column 34, line 4: Delete "800/a" and replace with -- 80% --

Column 34, line 7: Delete "900/a" and replace with -- 90% --

Column 34, line 11: Delete "UDP-GIcUA" and replace with -- UDP-GlcUA --

Column 34, line 11: Delete "UDP-GaINAc;" and replace with -- UDP-GalNAc; --

This certificate supersedes the Certificates of Correction issued July 20, 2010 and December 28, 2010.

Signed and Sealed this
First Day of March, 2011

David J. Kappos
*Director of the United States Patent and Trademark Office*